(12) United States Patent
Yao et al.

(10) Patent No.: US 7,449,558 B2
(45) Date of Patent: Nov. 11, 2008

(54) SITE-SPECIFIC LABELLING OF PROTEINS

(75) Inventors: Shao Qin Yao, Singapore (SG); Su-Yin Dawn Yeo, Singapore (SG)

(73) Assignee: National University of Singapore, Singapore (SG)

( * ) Notice: Subject to any disclaimer, the term of this patent is extended or adjusted under 35 U.S.C. 154(b) by 280 days.

(21) Appl. No.: 10/977,396

(22) Filed: Oct. 29, 2004

(65) Prior Publication Data
US 2005/0158804 A1 Jul. 21, 2005

Related U.S. Application Data

(60) Provisional application No. 60/515,418, filed on Oct. 30, 2003.

(51) Int. Cl.
*C07K 1/13* (2006.01)
(52) U.S. Cl. .................. 530/402; 530/407; 525/54.1; 514/2; 514/12; 435/7.5
(58) Field of Classification Search ................... 435/7.5
See application file for complete search history.

(56) References Cited

U.S. PATENT DOCUMENTS 5,834,247 A 11/1998 Comb et al.

OTHER PUBLICATIONS

Schwartz et al. 2003 "The splice is right": how protein splicing is opening new doors in protein science http://www.chemchannels.com/chemchannel/Archives/protein.htm.*
Tolbert et al. New Methods for Proteomic Research: Preparation of Proteins with N-Terminal Cysteines for Labeling and Conjugation. Angew. Chem. Int. Ed., (2002), 41, 2171-2174.*
Morrison et al. Intestinal Absorption of Captopril and Two Thioester Analogs in Rats and Dogs. Biopharmaceutics & Drug Disposition. 1998. vol. 18, Issue 1 , pp. 25-39.*
Stryler. Biochemistry, 1996 4th Ed. p. 8952.*
Keppler, A., et al. "A general method for the covalent labeling of fusion proteins with small molecules in vivo". Nature Biotechnology. Jan. 2003 (Epub Dec. 9, 2002). pp. 86-89. vol. 21, Issue 1.
Yeo, Dawn S.Y., et al. "Expanded Utility of the Native Chemical Litigation Reaction". Chem. Eur. J. 2004. pp. 4664-4672. vol. 10.
Kiick, Kristi L., et al. "Incorporation of azides into recombinant proteins for chemoselective modification by the Staudinger ligation". Proc. Natl. Acad. Sci. Jan. 8, 2002. pp. 19-24. vol. 99, Issue 1.

Tolbert, Thomas J., et al. "New Methods for Proteomic Research: Preparation of Proteins with N-Terminal Cysteines for Labeling and Conjunction". Angew. Chem. Int. Ed. 2002. pp. 2171-2174. vol. 41, Issue 12.
Schuler, Benjamin and Pannell, Lewis K. "Specific Labeling of Polypeptides at Amino-Terminal Cysteine Residues Using Cy5-benzyl Thioester". Bioconjugate Chem. 2002. pp. 1039-1043. vol. 13.
Griffin, B. Albert, et al. "Specific Covalent Labeling of Recombinant Protein Molecules Inside Live Cells". Science: Jul. 10, 1998. pp. 269-272. vol. 281.
Yeo, Dawn S.Y., et al. "Cell-permeable small molecule probes for site-specific labeling of proteins". Chemm Commum (Camb). Dec. 7, 2003. pp. 2870-2871. vol. 23.
"FIAsH-EDT2 Labeling Kit". Protein Labeling & Detection. Panvera. Invitrogen discovery screening. Jul. 7, 2003. file://WWYaolaptopWsyaoFIAsH-EDT2%20Labeling%20Kit.htm.
Baker, R.T. "Protein expression using ubiqutin fusion and cleavage". Curr. Opin. Biotechnol. 1996. pp. 541-546. vol. 7.
Chin, J.W., et al. "An Expanded Eukaryotic Genetic Code". Science. Aug. 15, 2003. pp. 964-967. vol. 301.
Dawson, P.E. and Kent, S.B.E. "Synthesis of Native Proteins by Chemical Ligation". Annu. Rev. Biochem. 2000. pp. 923-960. vol. 69.
Dawson, P.E., et al. "Synthesis of Proteins by Native Chemical Ligation". Science. Nov. 4, 1994. pp. 776-779. vol. 266.
Giriat, I. and Muir, T.W. "Protein Semi-Synthesis in Living Cells". J. Am. Chem. Soc. 2003. pp. 7180-7181. vol. 125.
Mahal, L.K., et al. "Engineering Chemical Reactivity on Cell Surfaces Through Oligosaccharide Biosynthesis". Science. May 16, 1997. vol. 276.
Saxon, E. and Bertozzi, C.R. "Cell Surface Engineering by a Modified Staudinger Reaction". Science. Mar. 17, 2000. pp. 2007-2010. vol. 287.
Lippincott-Schwartz, J. and Patterson, G.H. "Development and Use of Fluorescent Protein Markers in Living Cells". Science. Apr. 4, 2003. pp. 87-91. vol. 300.
Sun, W.C., et al. "Synthesis of Fluorinated Fluoresceins". J. Org. Chem. 1997. pp. 6469-6475. vol. 62.

(Continued)

*Primary Examiner*—L B Lankford
*Assistant Examiner*—Taeyoon Kim
(74) *Attorney, Agent, or Firm*—Klarquist Sparkman, LLP

(57) ABSTRACT

An in vivo method for labelling a protein having an N-terminal cysteine is disclosed. A probe comprising a thioester group and a detectable label is introduced into a cell expressing the N-terminal cysteine protein, allowing for the N-terminal cysteine to cleave the thioester bond and resulting in the label being covalently attached to the N-terminus of the protein by an amide bond.

12 Claims, 10 Drawing Sheets

OTHER PUBLICATIONS

Tsien, R.Y. "The Green Fluorescent Protein". Annu. Rev. Biochem. 1998. pp. 509-544. vol. 67.

Xu, M.Q. and Evans, T.C. "Intein-Mediated Ligation and Cyclization of Expressed Proteins". Methods. 2001. pp. 257-277. vol. 24.

Zhang, Z.W., et al. "A New Strategy for the Site-Specific Modification of Proteins in Vivo". Biochemistry. 2003. pp. 6735-6746. vol. 42.

Zhu, Q., et al. "Enzymatic Profiling System in a Small-Molecule Microarray". Organic Letters. 2003. pp. 1257-1260. vol. 5, No. 8.

Zhu, Q. et al. "Facile Synthesis of 7-Amino-4-carbamoylmethylcoumarin (ACC)-Containing Solid Supports and Their Corresponding Fluorogenic Protease Substrates". Bioorg. Med. Chem. Lett. 2003. pp. 1033-1036. vol. 13.

* cited by examiner

SEQUENCE LISTING

```
<160> NUMBER OF SEQ ID NOS: 8

<210> SEQ ID NO 1
<211> LENGTH: 42
<212> TYPE: DNA
<213> ORGANISM: artificial
<220> FEATURE:
<223> OTHER INFORMATION: synthetic oligonucleotide primer

<400> SEQUENCE: 1
ggtggttgct cttccaactg cagagccatg gtgagcaagg gc                    42

<210> SEQ ID NO 2
<211> LENGTH: 30
<212> TYPE: DNA
<213> ORGANISM: artificial
<220> FEATURE:
<223> OTHER INFORMATION: synthetic oligonucleotide primer
```

```
<400> SEQUENCE: 2
ggtggtctgc agttacttgt acagctcgtc                                    30

<210> SEQ ID NO 3
<211> LENGTH: 42
<212> TYPE: DNA
<213> ORGANISM: artificial
<220> FEATURE:
<223> OTHER INFORMATION: synthetic oligonucleotide primer

<400> SEQUENCE: 3
ggtggttgct cttccaactg cagagccatg tccctatac ta                       42

<210> SEQ ID NO 4
<211> LENGTH: 27
<212> TYPE: DNA
<213> ORGANISM: artificial
<220> FEATURE:
<223> OTHER INFORMATION: synthetic oligonucleotide primer

<400> SEQUENCE: 4
ggtggtctgc agtcagtcac gatgcgg                                       27

<210> SEQ ID NO 5
<211> LENGTH: 67
<212> TYPE: DNA
<213> ORGANISM: artificial
<220> FEATURE:
<223> OTHER INFORMATION: synthetic oligonucleotide primer

<400> SEQUENCE: 5
ggggacaagt ttgtacaaaa aagcaggctt cgaaggagat agaaccatgg ctatctctgg   60
cgatagt                                                             67

<210> SEQ ID NO 6
<211> LENGTH: 48
<212> TYPE: DNA
<213> ORGANISM: artificial
<220> FEATURE:
<223> OTHER INFORMATION: synthetic oligonucleotide primer

<400> SEQUENCE: 6
ggggaccact ttgtacaaga aagctgggtc ctgcagttac ttgtacag                48

<210> SEQ ID NO 7
<211> LENGTH: 30
<212> TYPE: DNA
<213> ORGANISM: artificial
<220> FEATURE:
<223> OTHER INFORMATION: synthetic oligonucleotide primer

<400> SEQUENCE: 7
ggtggtctgc agttatctag atccggtgga                                    30

<210> SEQ ID NO 8
<211> LENGTH: 48
<212> TYPE: DNA
<213> ORGANISM: artificial
<220> FEATURE:
<223> OTHER INFORMATION: synthetic oligonucleotide primer

<400> SEQUENCE: 8
ggggaccact ttgtacaaga aagctgggtc ctgcagttat ctagatcc                48
```

SITE-SPECIFIC LABELLING OF PROTEINS

CROSS-REFERENCE TO RELATED APPLICATION

The present invention claims priority from U.S. provisional patent application No. 60/515,418, filed on Oct. 30, 2003, which is hereby fully incorporated herein by reference.

FIELD OF THE INVENTION

The present invention relates generally to methods for labelling proteins.

BACKGROUND OF THE INVENTION

Studying the dynamic movement and interactions of proteins inside living cells is critical for a better understanding of cellular mechanisms and functions. Traditionally this has been done by in vitro labelling of proteins with fluorescent and other molecular probes, followed by transfer of the labelled protein into a live cell for real time monitoring, using advanced imaging techniques including confocal microscopy (G. T. Hermanson, *Bioconjugate Techniques*, Academic Press, San Diego, Calif., 1996).

Recent advances in genetic engineering have made it possible to directly generate fluorescently labelled proteins in living cells, or even live animals, by fusion of fluorescent proteins such as GFP (Green Fluorescent Protein) to the protein of interest (R. Y. Tsien, *Annu. Rev. Biochem.* (1998) 57: 509). Although this technique may be a quite powerful method of visualizing proteins in vivo, the fusion of GFP or other fluorescent proteins with a target protein may affect the target protein's biological and cellular activities, due to the relatively large size of the fusion (i.e. 27 KDa for GFP). Furthermore, there are currently few fluorescent proteins available, thereby limiting the number of colours that can be used to "tag" a protein in vivo. As well, this strategy is limited to labelling a target protein only with protein molecular labels, typically fluorophores, but not other molecular probes such as small molecule probes.

In order to address some of these problems, Tsien and colleagues recently described a novel method which allows efficient labelling of proteins in vivo using cell-permeable organoarsenic compounds (B. A. Griffin, S. R. Adams and R. Y. Tsien, *Science* (1998) 281: 269). This approach requires insertion of an alpha-helical -CCXXCC-motif into the target protein, typically at the N- or C-terminus or at a surface-exposed region of the protein, for covalent binding with the organoarsenic compound. The introduction of such a motif has the potential to disrupt the native folding of the target protein. Furthermore, this method may result in background labelling, making it difficult to detect labelled target protein if expressed at low levels.

Johnsson and colleagues described enzyme-catalysed, in vivo labelling of proteins fused to the human DNA repair protein hAGT (A. Keppler, S. Gendreizig, T. Gronemeyer, H. Pick, H. Vogel and K. Johnsson, *Nat. Biotechnol.* (2003) 21:86-89). This approach also results in the introduction of a macromolecular fusion into the target protein, potentially perturbing the native function of the protein.

Other in vivo-compatible chemical reactions, including the ketone-hydrazine reaction (Mahal, L. K., Yarema, K. J. & Bertozzi, C. R. *Science* (1997) 276:1125-1128; Zhang, Z. W., Smith, B. A. C., Wang, L., Brock, A., Cho, C. & Schultz, P. G. *Biochemistry* (2003) 42:6735-6746), and the Staudinger reaction (Saxon, E. & Bertozzi, C. R. *Science* (2000) 287: 2007-2010), have been successfully used for in vivo labelling of biomolecules. However, these methods require the introduction of non-natural occurring functionalities into the target biomolecule in vivo, and thus are useful for only limited applications, for example cell surface engineering and labelling of membrane proteins.

Methods for protein labelling based on the addition of unnatural amino acids to the genetic code of *Saccharomyces cerevisiae* or *Escherichia coli* have been described (Chin, J. W., Cropp, T. A., Anderson, J. C., Mukherji, M., Zhang, Z. & Schultz, P. G. *Science* (2003) 301:964-967; Kiick, K. L., Saxon, E., Tirrell, D. A. & Bertozzi, C. R. *Proc. Natl. Acad. Sci. USA* (2002) 99:19-24). These methods may be complicated to use in that they require genetic manipulation of the host cellular expression system used to express the target protein.

SUMMARY OF THE INVENTION

In one aspect, the present invention provides a method for labelling a protein in a cell, comprising introducing a detectable probe having a thioester group into a cell expressing a protein having an N-terminal cysteine.

In another aspect, the present invention provides a method for visualizing a protein in a cell, comprising introducing a detectable probe having a thioester group into a cell expressing a protein having an N-terminal cysteine; and observing the cell under conditions in which the detectable probe may be visualized.

In a further aspect, the present invention provides a method for isolating a protein from a cell, comprising introducing a detectable probe having a thioester group into a cell expressing a protein having an N-terminal cysteine; lysing the cell; and capturing the detectable probe.

Other aspects and features of the present invention will become apparent to those of ordinary skill in the art upon review of the following description of specific embodiments of the invention in conjunction with the accompanying figures.

BRIEF DESCRIPTION OF THE DRAWINGS

In the figures, which illustrate, by way of example only, embodiments of the present invention.

DETAILED DESCRIPTION

Figure 1:
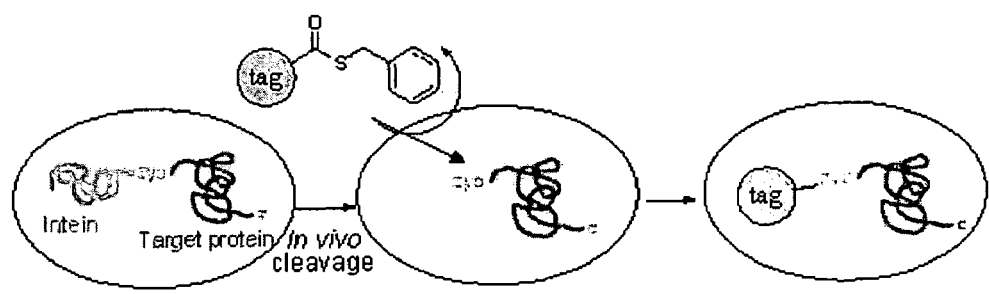
FIG. 1 is a schematic diagram of one embodiment of the present method.

By selectively labelling proteins in vivo, it becomes possible to visualize protein localization and movement within a live cell, to detect protein-protein interactions within a live cell and to determine protein expression patterns in response to varied growth and environmental conditions and stresses. The chemoselective reaction between a thioester-containing small molecule and an N-terminal cysteine protein as described herein provides a novel strategy for site-specific covalent labelling of proteins in vivo. When a cell-permeable thioester probe is introduced into cells expressing a protein having an N-terminal cysteine, a covalent reaction between the thioester probe and the N-terminal cysteine occurs within the cell, as set out in the schematic diagram of FIG. 1.

With the use of a cell-permeable probe, it is possible to easily introduce the probe into the cell, with minimal manipulation of the cell, minimizing the need for genetic manipulation or the introduction of additional exogeneous factors.

A protein having a cysteine as the N-terminal amino acid is referred to herein as an "N-terminal cysteine protein" or as a "protein having an N-terminal cysteine". Such proteins have previously only been used to site-specifically label proteins in vitro (P. E. Dawson and S. B. Kent, Annu. Rev. Biochem. (2000) 69:923; T. J. Tolbert and C. H. Wong, Angew. Chem. Int. Ed. (2002) 41:2171; B. Schuler and L. K. Pannell, Bioconj. Chem. (2002) 13:1039), or in ex vivo protein semi-synthesis reactions (I. Giriat and T. W. Muir, J. Am. Chem. Soc. (2003) 125:7180). The method described by Giriat and Muir relies on the conjugation of molecular tags ex vivo to a peptide, and subsequent delivery of the conjugate to the cell by injection or by the use of protein transduction domains (PTDs), greatly limiting its application for potential in vivo protein modifications.

Figure 2:
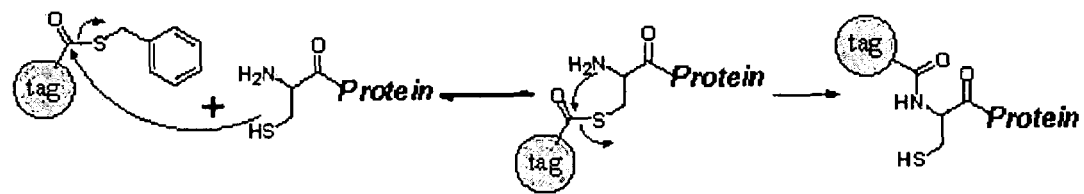
FIG. 2 is a schematic diagram showing the reaction between a thioester-containing compound and an N-terminal cysteine protein.

Briefly, the thioester bond of the probe is selectively cleaved by the thiol-containing N-terminal cysteine protein to form a new thioester bond between the sulfur atom of the cysteine and the carbonyl group of the original thioester group of the probe. Under circumstances where a primary amino group is in proximity to the newly formed thioester bond, as is the case in cysteine, the newly formed thioester bond may undergo spontaneous acyl rearrangement with the amino group so as to form an amide bond and a free thiol group, as set out in FIG. 2.

The presence of a single cysteine residue at the N-terminus of the protein of interest allows for the in vivo labelling of the protein with a probe by covalent attachment at the N-terminus via a native peptide linkage. This method of labelling therefore should result in minimal disruption of the native conformation of the protein of interest. The labelled proteins may then be readily visualized while inside a live cell.

Furthermore, the proteins labelled in vivo may be isolated from cells once lysed, which is useful for quantification of protein expression levels and for detecting proteins that may interact with the labelled protein of interest, for example by using capture assays such as immunoprecipitation assays.

The chemoselective reaction in vivo can be highly selective, with little background, since endogenous N-terminal cysteine proteins are rare. A ScanProsite (ExPASy) search of known bacterial and mammalian genomes revealed that there are few endogeneous N-terminal cysteine proteins, of which most are already disulfide-bonded with other internal cysteine residues, thus making them unreactive toward thioester probes. The presence of other reactive amino acid side chains, including internal cysteines, does not prevent the exclusive formation of a stable amide bond between the N-terminal cysteine moiety on the protein and the thioester-containing probe. As well, thiol-containing molecules that are abundant in cells, e.g. glutathione, are inert to the thioester probes as well (Yeo S. Y. D. et al., Chem. Commun. (2003) 23: 2870-2871; Dawson, P. E., Muir, T. W., Clark-Lewis, I., & Kent, S. B. H. Science (1994) 266: 776-779). Thus, the chemoselective reaction occurs predominantly between the thioester in the probe and the N-terminal cysteine of the protein. Other endogenous molecules, such as cysteine and cystamine, are present in the cell and are available to also react with the probe. However, their reaction products are also small molecules in nature, and can be easily removed, together with any excessive unreacted probe, by washing of the cells after labelling.

Thus, a protein of interest having an N-terminal cysteine expressed inside a live cell can be selectively labelled with a thioester containing probe. The cell may be a prokaryotic or a eukaryotic cell in which it is desired to express the protein of interest. As will be understood, "a cell" refers to a single cell, a cell line, or a population of cells derived from the same progeny cell. As well, the term "a protein" as used herein includes singular and plural contexts unless indicated otherwise.

The expression of a protein of interest within a cell can be readily effected using known methods, for example as described in standard molecular biology manuals and texts such as Sambrook et al. in Molecular Cloning: A Laboratory Manual, 3$^{rd}$ Edition, Cold Spring Harbour, Laboratory Press and may require the cloning of the gene encoding the protein into a suitable expression vector. The expression vector can include a promoter region compatible with the cell in which the protein is to be expressed, operably linked to the gene encoding the protein of interest. The promoter region may be a low-level or high-level constitutive promoter, or an inducible promoter. If the protein is an endogenous protein, it may be desirable to use the native promoter region for the gene encoding the protein, so as to mimic natural expression levels and patterns in the cell.

Depending on the desired utility, the protein of interest may be expressed as a fusion protein or a chimeric protein. However, if the protein of interest is to be studied in a state most closely resembling its natural state, it is preferred that any additional amino acids, except for the N-terminal cysteine residue, be cleaved during the generation of the N-terminal cysteine protein, for example, as with the intein fusion method, described below.

Any N-terminal cysteine protein of interest may be generated and expressed in a cell by methods known in the art. Various approaches are known in the art, and include ubiquitin-fusion methods, site-specific protease digestion and intein-mediated methods, each of which is described herein.

For example, in a eukaryotic system having endogenous de-ubiquitinating enzymes, the protein of interest may be expressed as a fusion protein with ubiquitin, such that the protein of interest is fused immediately C-terminal to the last residue of ubiquitin and the first residue in the protein of interest is a cysteine residue. The endogenous enzymes will cleave the fusion immediately C-terminal to ubiquitin, yielding the N-terminal cysteine protein of interest, having only the additional cysteine residue added to the N-terminus of the protein of interest (Baker, R. T. *Curr. Opin. Biotechnol.* (1996) 7: 541.). This approach has the advantage of only requiring engineering and expression of the ubiquitin fusion protein, since the cleavage enzymes are naturally produced by the cell.

A skilled person will understand how to engineer and express the protein of interest as a ubiquitin fusion, with a cysteine residue between the last ubiquitin residue and the first methionine residue of the protein of interest. Generally, an appropriate expression vector that is compatible with the cell in which the protein is to be expressed, as described above, and containing the ubiquitin gene under control of the desired promoter, will be used to express the protein of interest as a ubiquitin-cysteine-protein of interest construct.

Alternatively, the N-terminal cysteine protein may be generated by selective proteolysis. For example, the protein of interest may be engineered to have a recognition sequence for a site-specific protease at its N-terminus, which protease cleaves the fusion protein to yield an N-terminal cysteine residue. As stated above, it is usually preferred that no additional amino acid residues are incorporated into the final N-terminal cysteine protein, except for the necessary cysteine residue. When using this approach, a skilled person will understand how to design an appropriate expression vector so as to result in the expression of the protein of interest having the additional protease recognition sequence immediately adjacent to a cysteine residue, followed by the native protein sequence.

Examples of suitable proteases include Factor Xa and TEV (tobacco etch virus) NIa protease (Tolbert, T. J. & Wong, C. H. *Angew. Chem. Int. Ed.* (2002) 41:2171-2174). TEV NIa protease is preferred, since Factor Xa is not entirely sequence specific and which therefore could result in non-specific cleavage of proteins in the cell other than at the target site at the N-terminus of the N-cysteine protein. If the protease in not normally expressed in the cell in which the N-terminal cysteine protein is expressed, then an expression vector designed to express the relevant protease can be transformed or transfected into the cell, using standard molecular biology techniques.

Another example of a method that may be used to generate an N-terminal cysteine protein in vivo is intein-mediated protein cleavage (Xu, M. Q and Evans, T. C. *Methods* (2001) 24:257-277). Generally, inteins are intervening protein sequences that are cleaved from a protein by undergoing native chemical ligation reactions. Intein-mediated approaches have previously been used to generate C-terminally labelled proteins using a protein-mutated intein fusion construct and a thiol-containing probe, as described in currently co-pending U.S. patent applications filed Jun. 30, 2003 and Jul. 6, 2004.

Certain inteins will undergo self-cleavage without any external co-factors required, for example, the Ssb DNA B mini-intein and the Sce VMA, Mxe and Mth inteins. In the present method, the protein of interest having an N-terminal cysteine may be fused to the C-terminus of a self-cleavable intein sequence. An internal cleavage reaction occurs between the last residue of the intein sequence and the first residue of the protein of interest (here designed to be cysteine), yielding cleaved N-terminal cysteine protein. Vectors for expressing proteins fused to a self-cleavable intein are commercially available, for example the PTWIN™ vectors from New England Biolabs. Further, a skilled person will understand how to design a suitable expression vector, using standard cloning and molecular biology techniques, to express the N-terminal cysteine protein as a cleavable intein-N-terminal cysteine protein fusion.

The intein-mediated protein cleavage approach for generating an N-terminal cysteine protein is preferred, as the N-terminal cysteine protein is generated via an autocatalytic process, eliminating the need for introduction of any external factors such as proteases into the host cell. This intein cleavage reaction is fairly efficient, and may yield as much as between 50% and 90% cleaved N-terminal cysteine protein under optimised conditions. A preferred intein is the Ssb DNA B mini-intein, although any intein that will undergo cleavage to yield the N-terminal cysteine protein without any spliced protein sequence at the N-terminus may be used.

A skilled person will understand that other methods that result in a protein construct that can be modified in the cell to generate an N-terminal cysteine protein can be used. Generally, an expression vector including a coding region for the N-terminal cysteine protein, including the expression vectors described above, may be produced using known molecular cloning techniques. The coding region may be produced, for example, using PCR site-directed mutation and amplification techniques, and inserted into a relevant cloning site in a vector using, for example, restriction enzyme and ligation methods. Using such methods, a vector can be constructed that will result in the expression in the cell of a protein construct that may then be processed within the cell to generate the N-terminal cysteine protein.

In order for the N-terminal cysteine to be expressed in the cell, the expression vector designed to express the protein of interest in a form suitable for generating the N-terminal cysteine protein, may be introduced into a cell by known methods, for example by transforming or transfecting the cell with the expression vector, or by microinjection techniques.

To label the expressed N-terminal cysteine protein in vivo a thioester probe is introduced into the cell expressing the N-terminal cysteine protein. A "thioester probe" can be any molecule that includes a thioester group and a detectable tag or label. The thioester group acts as the electrophilic reaction center for attack by the free thiol of the N-terminal cysteine of the protein. Thus, the term "detectable probe" is used herein to describe, and interchangeably with, "thioester probe". The detectable tag or label refers to, any tag or label that can be detected by any means, directly or indirectly, for example by using visualizing methods, autoradiography methods, colour development methods or by affinity binding. For example, the tag or label may comprise a fluorescent group, a chemiluminescent group, a radioactive group, a ligand for example biotin, a photolabile fluorescent group, a reactive group for example a protein cross-linker such as benzophenone, an antigen or an epitope, a paramagnetic group, or a heavy metal complex or moiety. The fact that the chemical attachment of the thioester probe to the protein involves the thioester as a reactive center, and is not dependent on the characteristics of the tag, allows for use of a wide range of possible tags or labels, including a variety of different fluorophores each of which may fluoresce at a characteristic wavelength. Preferably, the tag or the label selected does not interfere with the biological function of the protein to which it will be attached.

As can be appreciated, the detectable tag or label is located adjacent to the carbonyl side of the thioester bond, so that upon cleavage of the thioester bond by the N-terminal cysteine, the tag or label will be covalently attached to the N-terminus of the protein via an amide bond.

The thioester probe is preferably cell-permeable, meaning that the thioester probe is able to permeate through the cell membrane, allowing it to come in contact with the expressed N-terminal cysteine protein. A skilled person can readily prepare thioester probes that are cell-permeable, and will understand for example that uncharged, hydrophobic molecules are more readily able to permeate the cell membrane and that the probe should be sufficiently small to allow the probe to permeate the cell membrane. For example, the thioester probe may be designed to have a hydrophobic group adjacent to the thio side of the thioester group, such as a benzyl group, to increase the cell-permeability of the probe. A skilled person will appreciate that a hydrophobic group attached to the thio side of the thioester group will be released from the probe upon cleavage of the thioester bond by the N-terminal cysteine, and that the hydrophobic group chosen should be such that it will not interfere with the cleavage of the thioester bond by the N-terminal cysteine.

Figure 3:
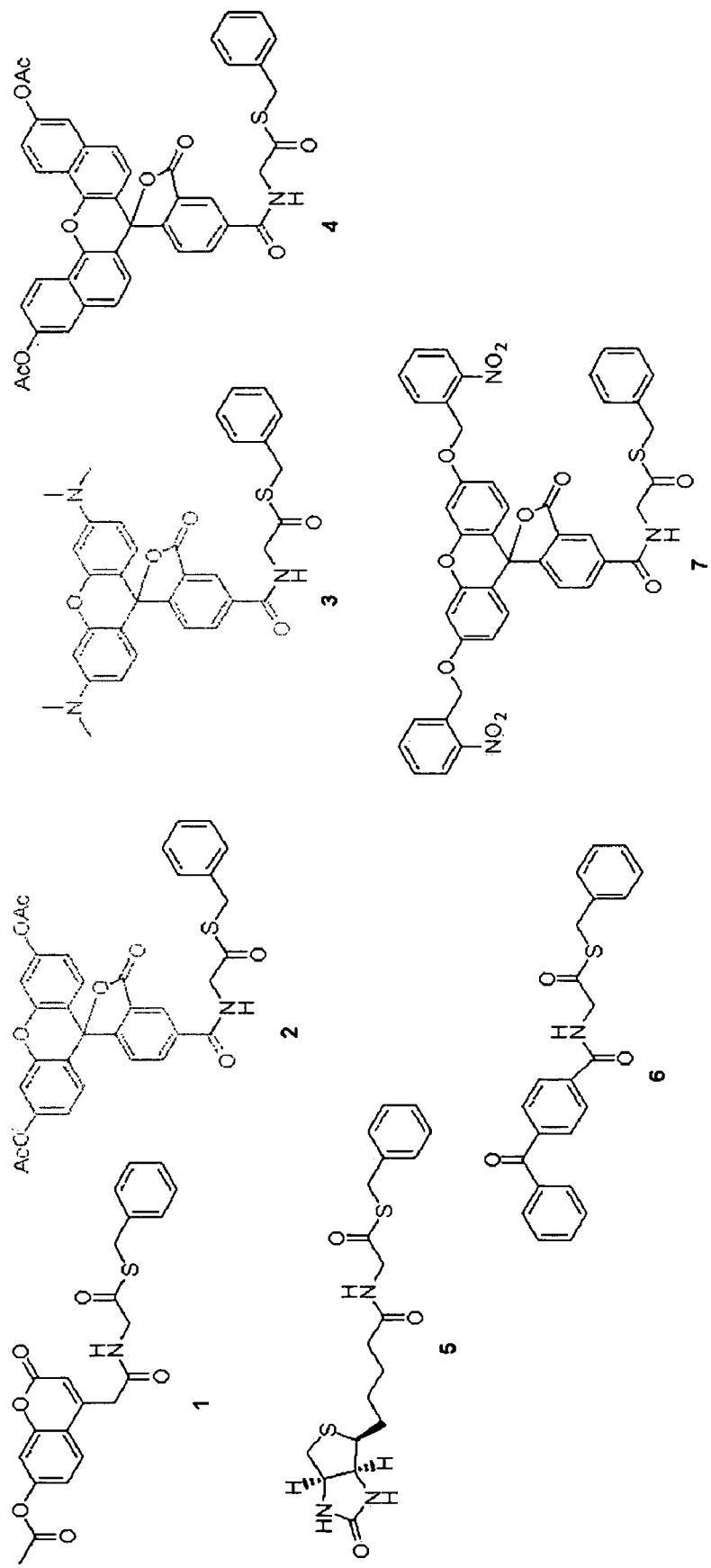
FIG. 3 is a schematic diagram depicting the chemical structures of various probes useful for labelling proteins having an N-terminal cysteine.

Preferably, the thioester probe is a small detectable compound which has been modified to include a thioester group. For example, the thioester probe may be a fluorophore that has been modified to have a thioester group, or it may be a ligand, for example biotin, modified to include a thioester group. The invention therefore provides a detectable thioester probe which is cell permeable, and which therefore can be used to detectably label an N-terminal cysteine protein in vivo. In different embodiments, the thioester probe may be acetic acid 4-[-(benzylsulfanylcarbonylmethyl-carbamoyl)-methyl]-2-oxo-2H-chromen-7-yl ester; N-benzylsulfanyl-carbonylmethyl-6-(3,6-dihydroxy-3H-xanthen-9-yl)-isophthalamic acid; amino thioacetic acid S-benzyl ester of 5-carboxy-tetramethylrhodamine; amino thioacetic acid S-benzyl ester of acetoxynapthofluorescein; [5-(2-oxo-hexahydro-thieno[3,4-d]imidazol-6-yl)-pentanoylamino]-thioacetic acid S-benzyl ester; (4-benzoyl-benzoylamino)-thioacetic acid S-benzyl ester; or amino thioacetic acid S-benzyl ester of caged fluorescein. Structures of these probes are shown in FIG. 3, and synthesis pathways are described in the Examples given below.

A skilled person will understand how to synthesize a detectable thioester probe using standard chemistry methods, for example by converting a succinimidyl ester of a suitable tag or label into a benzyl thioester by common synthetic methods, such as simple treatments with a suitable thiol containing reagents as described in Yeo S. Y. D. et al., *Chem. Commun.* (2003) 23: 2870-2871, or with trimethyl aluminium-activated benzyl mercaptan, as described in Schuler and Pannell, *Bioconjug Chem*. (2002) 13:1039-1043.

Depending on the desired purpose, the thioester probe may include a specific type of tag or label on the carbonyl side of the thioester. For example, if the protein of interest is to be visualized within a live cell, a tag that is visible in the cell may be used, such as a fluorescent or chemiluminescent label. If temporal visualization is required, a photolabile fluorescent tag may be used, that may be photolysed at a desired time or under certain growth conditions.

If protein-protein interactions are to be studied, the tag or label may be one that allows for capture of the protein from a cell lysate, such as a ligand, an antigen or an epitope, or one that allows for protein cross-linking, such as a reactive group that can be activated to cross-link with functional groups found in proteins. Alternatively, a fluorescent label may be used, if potential protein interaction partners are also labelled with a different fluorescent label, and the two fluorescent labels form a donor-acceptor pair to allow for fluorescence resonance energy transfer (FRET), as will be understood by a skilled person.

If expression profiles are to be studied, or protein expression levels under certain growth conditions are to be quantified, then a tag that allows for identification of the protein of interest in a cell lysate may be used, for example, a radioactive group, a chemiluminescent group or a heavy metal complex.

To introduce a cell permeable thioester probe into the cell, the thioester probe may be added to the growth or culture medium of the cell at a desired point in the growth of curve of the cell, and the cell grown for a further amount of time to allow for the thioester probe to enter the cell and react with expressed N-terminal cysteine protein. A skilled person will be able to determine the optimal conditions required to introduce the probe for efficient labelling of a given N-terminal cysteine protein in a particular cell type, for example by performing routine time-course experiments. In different embodiments, the probe is added to the growth or culture medium for about 1 to about 24 hours, or for about 3 to about 8 hours.

The amount of thioester probe added will depend in part on the cell-permeability of the thioester probe in the particular cell being used to express the N-terminal cysteine protein, as well as on the level of protein that is expressed. A skilled person will be able to determine the concentration of thioester probe required to optimize the labelling of the N-terminal cysteine. For example, if the thioester probe is added to a liquid culture in which the cell is grown, it may be added at a final concentration of about 1 µM to about 1 mM, or about 5 µM to about 100 µM. Enough thioester probe should be added to allow for an efficient reaction between the thioester group of the probe and the N-terminal cysteine of the protein, while minimizing non-specific reactions and avoiding toxic effects on the cells.

Any excess thioester probe and non-specific reaction product, meaning products of a reaction with a cysteine other than in the protein of interest, can be removed by washing the cell in a solution free of thioester probe, so as to leach unreacted thioester probe and non-specific reaction products from the cell. Multiple solution changes can increase the amount removed, thereby decreasing background created by the presence of unreacted tag or non-specific reaction products in the cell. The solution used for washing may be a buffer, growth medium, or any solution that is isotonic with respect to the cells in order to prevent lysis of the cells during washing. A skilled person can readily determine suitable washing conditions required to minimize the background.

If desired, intact cells may be visualized in order to detect the N-terminal cysteine protein when labelled with a visible tag or label, for example, using fluorescence microscopy techniques to detect a fluorescent label. A skilled person will be familiar with such visualization techniques and understand that any given fluorophore will have a particular wavelength at which it should be viewed. Such visualization will identify the location of the N-terminal cysteine protein within the cell. By monitoring cell cycle timing, or by varying environmental conditions, it is possible to use this technique to observe a varying expression profile for an N-terminal cysteine protein of interest. Depending on the amount of probe used, and the resulting background levels within the cell due to unreacted probe or non-specific reaction products, as well as on the amount and localization of labelled N-terminal cysteine protein, it may be desirable to wash the cells prior to visualizing. However, if the background levels are sufficiently low, a skilled person will appreciate that washing the cells to reduce background may not be necessary.

If desired, the cell may be lysed using standard techniques such as sonication, enzymatic digestion or high pressure disruption, to isolate the protein of interest. If the protein of interest is labelled with an affinity group, such as a ligand or antigen, the labelled N-terminal cysteine protein may be captured from the cell lysate, using standard techniques known in the art, such as affinity chromatography, and precipitation assays. For example, the protein may be labelled with a probe containing a biotin moiety, and captured using immobilized avidin or streptavidin. Proteins isolated in this manner are useful to study protein-protein interactions, for example, by performing an immunoprecipitation or pull-down assay so as to identify proteins that can be co-isolated with the N-terminal protein of interest. As discussed above, the cells may be washed prior to lysis to minimize background.

The cell lysate may also be visualized, for example by using standard SDS-PAGE and Western blotting techniques, to monitor the expression profile of the protein of interest in response to varying growth conditions. If a tag such as a chemiluminescent group, a radiolabel or an antigen is used, the N-terminal cysteine protein of interest may be easily identified by exposing a separated lysate to x-ray film.

All documents referred to herein are fully incorporated by reference.

Although various embodiments of the invention are disclosed herein, many adaptations and modifications may be made within the scope of the invention in accordance with the common general knowledge of those skilled in this art. Such modifications include the substitution of known equivalents for any aspect of the invention in order to achieve the same result in substantially the same way. All technical and scientific terms used herein have the same meaning as commonly understood by one of ordinary skill in the art of this invention, unless defined otherwise.

EXAMPLES

Generally, all chemicals were purchased from commercial sources, unless indicated otherwise. All chemical reactions were run under $N_2$, unless otherwise indicated. The $^1H$ and $^{13}C$ NMR spectra were taken on a Bruker 300 MHz spectrometer. Chemical shifts are reported in parts per million referenced to internal standard $((CH_3)_4Si=0.00$ ppm). The mass spectra were taken on a Finnigan LCQ spectrometer.

Example 1

Synthesis of Membrane-Permeable Thioester Containing Probes

A total of 7 different thioester-containing probes were synthesized for in vivo protein labelling at N-terminal cysteines, the various structures of which are depicted in FIG. 3. Probes 1 to 4 are fluorophore-containing thioesters; 5 and 6 are biotin- and benzophenone-containing probes, respectively; 7 is a "caged" molecule of 2, in which the fluorescence is designed to be "turned on" selectively upon photolysis. All probes were designed to be cell-permeable: acetates of different fluorophores were incorporated in 1, 2 and 4 to increase their cell permeability. The fluorophore in 3, tetramethylrhodamine (TMR), as well as the biotin and benzophenone moieties in 5 and 6, respectively, were previously shown to be cell-permeable (R. P. Haugland, *Handbook of fluorescent probes and research products*, 9th Ed, Molecular Probes: Eugene, Oreg., 2002). The hydrophobic, benzyl-based thioester moiety in all 7 probes should further assist in cell permeability.

Figure 4A:
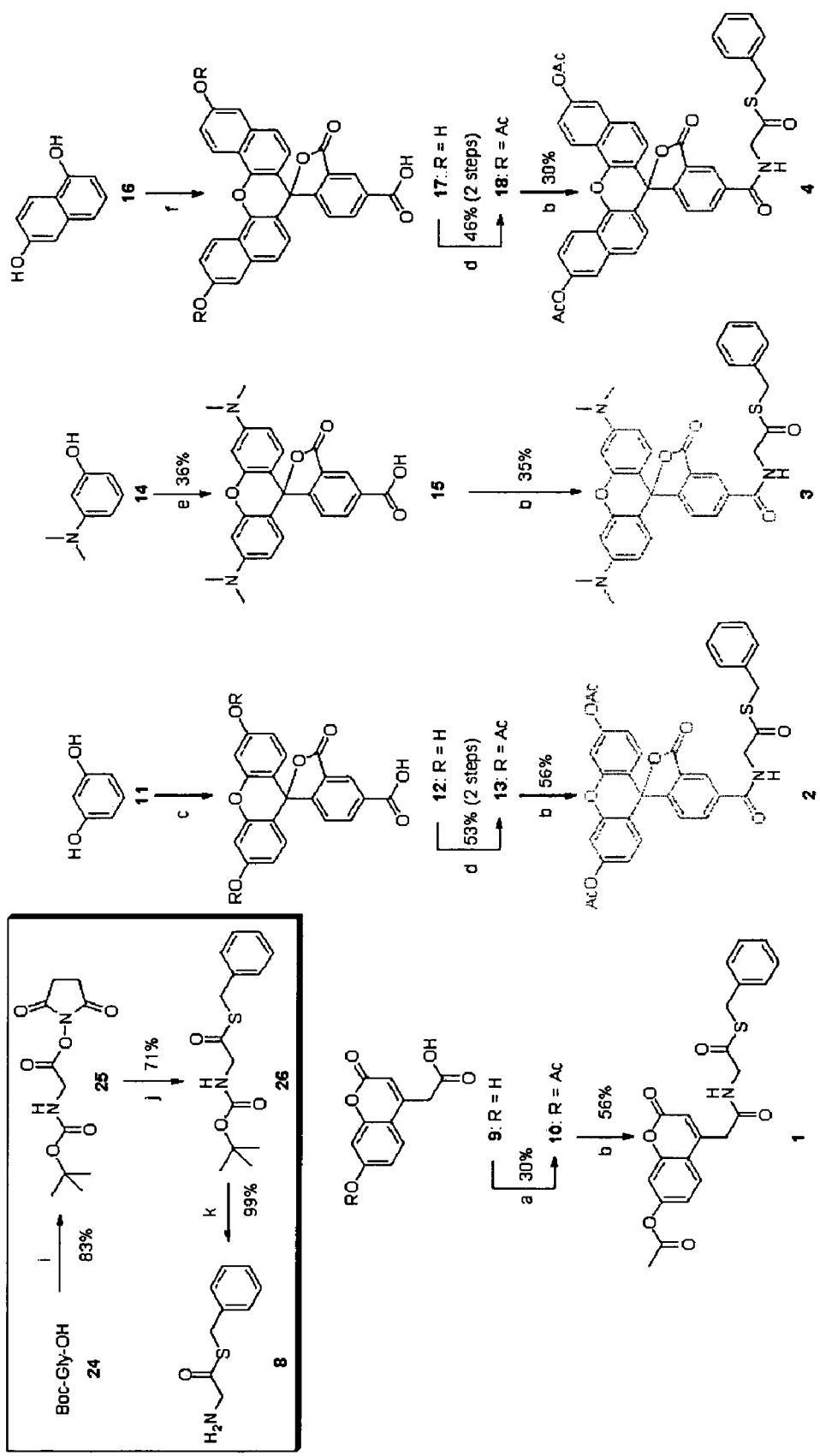
FIG. 4 is a schematic diagram depicting the synthesis reactions used to synthesize various probes.
Figure 4B:
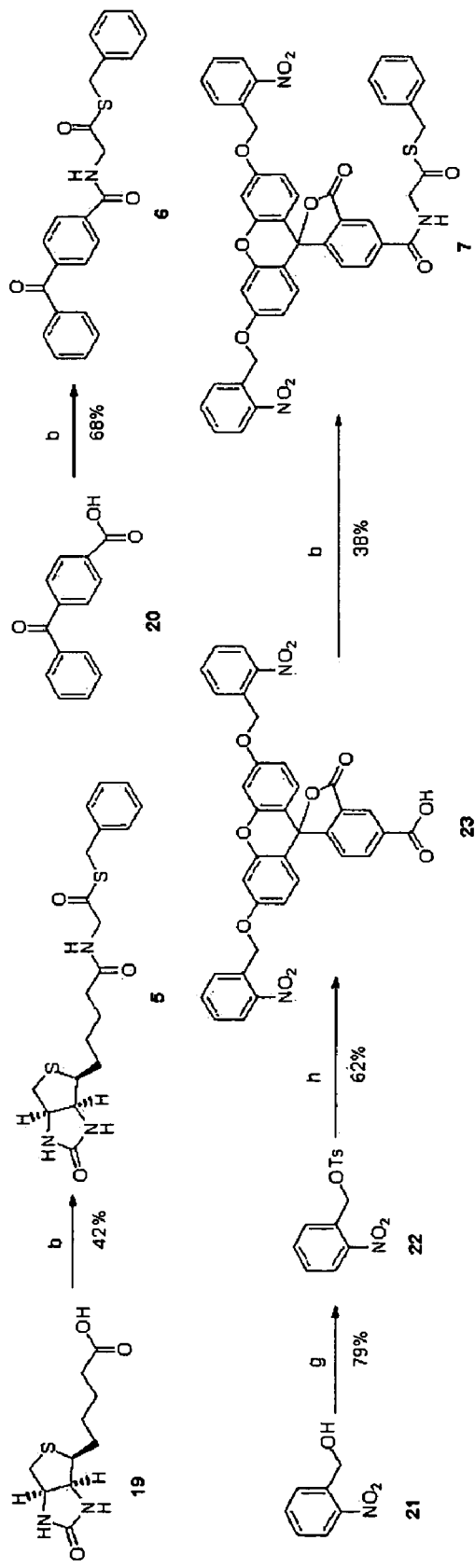

The probes were synthesized as described below, and as shown in the schematic of FIG. 4. As indicated, the reagents and conditions used were (a) $Ac_2O$, pyridine, 30 min, RT; (b) 8, EDC, HOBt, THF/DMF, RT; (c) trimellitic anhydride, $CH_3SO_3H$, 80° C., 12 h; (d) $Ac_2O$, pyridine, 15 min, 85° C.; (e) trimellitic anhydride, toluene, 110° C., 12 h; (f) trimellitic anhydride, $CH_3SO_3H$, 100° C., 12 h; (g) p-toluenesulfonyl chloride, DCM, RT, 2 h; (h) 12, $K_2CO_3$, DMF, 60° C., 6 h; (i) N-hydroxysuccinimide, DCC, THF, RT, 1 h; (j) benzyl mercaptan, THF, RT, 12 h; (k) 4 N HCl, dioxane, RT, 2 h.

Probe 1 was readily synthesized from CM 9, which was prepared as previously reported (Zhu, Q. et al., *Org. Lett.* (2003) 5: 1257-1260; Zhu, Q. et al., *Bioorg. Med. Chem. Lett.* (2003) 13: 1033-1036.). Acetylation of 9 gave 10 in 30% yield, which was then converted to 1 (56% yield) by coupling to thioester 8 under mild conditions. Neutralizing bases (i.e. DIEA) commonly used in the coupling reaction should be avoided, as the diacetates in 1, 2 & 4 are extremely base-labile. For the same reason, base extraction (e.g. $NaHCO_3$) in the workup should also be avoided. The other three dyes, FL 12, TMR 15 and CF 17, are all commercially available but were conveniently synthesized in-house using optimized procedures. 12 was prepared from resorcinol 11 and trimellitic anhydride in the presence of methanesulfonic acid, following published protocols (Sun, W. C.; Gee, K. R.; Klaubert, D. H.; Haugland, R. P. *J. Org. Chem.* (1997) 62: 6469-6475.). Following acetylation, the resulting product, 13 upon purification, was coupled with 8 to give probe 2 in 56% yield (in 2 steps). 15 and 17 were similarly prepared. By adjusting the reaction conditions (e.g. temperature, time, solvent, $CH_3SO_3H$) used in the FL synthesis, both TMR and CF dyes could also be conveniently obtained in high yields from their respective starting materials (i.e. 14 and 16). Subsequently, 15, and the corresponding acetylated product of the CF dye, 18, were similarly coupled with 8 to give probes 3 and 4, respectively. Probes 5 and 6 were prepared in one step by coupling commercially available starting materials, 19 and 20, with the thioester 8, respectively. The "caged" probe 7 was generated similarly from 23, which was readily prepared from 12 by masking the two phenolic alcohols with o-nitrobenzyl alcohol 21.

Preparation of tert-Butoxycarbonylamino-acetic acid 2,5-dioxo-pyrrolidin-1-yl ester (25): Commercially available Boc-glycine-OH, 24 (7.0 g, 40 mmol) was dissolved in 60 mL of dry THF at 0° C. To this solution was added DCC (4.6 g, 40 mmol) and the mixture was stirred at RT for 1 hour. Upon filtration to remove the precipitate, the resulting product was concentrated under reduced pressure. Pure crystals of 25 (9.03 g, 83%) was obtained by recrystallization with hot isopropanol.
$^1$H-NMR (300 MHz, CDCl$_3$) δ 7.2 (broad, 1H), 4.28 (d, J=5.22 Hz, 2H), 2.84 (s, 4H), 1.46 (s, 9H). MS (ESI): m/z 294.9 [(M+Na)]$^+$.

Preparation of tert-Butoxycarbonlyamino-thioacetic acid S-benzyl ester (26): 25 (10 g, 36.73 mmol) was dissolved in dry THF. DIEA (6.8 ml, 38.7 mmol) was added followed by benzyl mercaptan (4.67 ml, 38.7 mmol). The resulting mixture was stirred at RT for overnight. Upon evaporation to dryness, the product was redissolved in ethyl acetate, washed with 2×1 N HCl, 2×Sat. NaHCO$_3$, water and brine. The organic layer was dried with anhydrous MgSO$_4$. The resulting white solid was dissolved in a minimal amount of DCM and recrystallized with hexane to afford 26 (7.3 g, 71%). $^1$H-NMR (300 MHz, CDCl$_3$) δ 7.29-7.26 (m, 5H), 4.14 (s, 2H), 4.06 (d, J=5.61 Hz, 2H), 1.45 (s, 9H). MS (ESI): m/z 304.1 [(M+Na)]$^+$.

Preparation of amino thioacetic acid S-benzyl ester (8): 26 (7.3 g, 26 mmol) was dissolved in 4 N HCl (20 ml) and dioxane (20 ml), followed by stirring at RT for 2 hours. The solution was then concentrated in vacuo and chased with ether (3×50 ml) to afford pure white crystals of 8 (4.67 g, 99%). $^1$H-NMR (300 MHz, DMSO) δ 8.5 (broad, 3H), 7.29-7.33 (m, 5H), 4.25 (s, 2H), 4.08 (s, 2H). $^{13}$C-NMR (60 MHz, DMSO) δ 192.70, 136.89, 128.79, 128.50, 127.32, 46.72, 32.09. MS (ESI): m/z 182.0 [(M+1)]$^+$.

Preparation of 7-Hydroxycoumarin-4-acetic acid (9): Resorcinol (5 g, 45 mmol) was dissolved in 50 ml of 70% H$_2$SO$_4$ under ice-cold conditions, and the solution was allowed to stir for 30 minutes. Acetone carboxylic acid (6.6 g, 45 mmol) was added in 5 portions. The mixture was allowed to stir further for 4 hrs, before pouring onto crushed ice pieces. The precipitate formed was washed with water, ethyl acetate and dried overnight under reduced pressure to afford a pure white solid (9 g, 91%). $^1$H NMR (300 MHz, DMSO) δ 7.53 (d, J=9.1 Hz, 1H), 6.80 (dd, J=8.7 & 2.1 Hz, 1H), 6.73 (d, J=2.1 Hz, 1H), 6.22 (s, 1H), 3.82 (s, 2H). $^{13}$C-NMR (60 MHz, DMSO) δ 170.56, 161.10, 158.16, 154.94, 150.05, 127.65, 126.58, 112.93, 111.90, 102.23, 39.30. MS (ESI): m/z 221.0 [(M+1)]$^+$.

Preparation of 7-Acetoxycoumarin-4-acetic acid (10): To 9 (1 g, 4.53 mmol) was added 25 ml of acetic anhydride and 5 ml of pyridine, and the reaction was allowed to stir at RT for 30 minutes. Upon removal of solvent in vacuo, the residue was taken into ethyl acetate and washed with 1 N HCl (2×30 ml), water (2×30 ml) and brine (2×30 ml). The organic layer was dried over anhydrous Na$_2$SO$_4$ and concentrated in vacuo to afford 10 (30% yield). $^1$H NMR (300 MHz, CDCl$_3$) δ 7.71 (d, J=8.9 Hz, 1H), 7.23 (d, J=5.6 Hz, 1H), 7.24 (s, 1H), 6.47 (s, 1H), 2.94 (s, 2H), 2.33 (s, 3H). MS (ESI): m/z 263.0 [(M+H)]$^+$.

Preparation of acetic acid 4-[-(benzylsulfanylcarbonylmethyl-carbamoyl)-methyl]-2-oxo-2H-chromen-7-yl ester (1): To a solution of 10 (0.162 g, 0.62 mmol) in dry THF was added EDC (0.13 g, 0.68 mmol) and HOBt (0.104 g, 0.68 mmol). The reaction was stirred for 30 minutes under ice-cold conditions, followed by addition of 8 (0.135 g, 0.62 mmol) dissolved in minimal amount of DMF. The resulting solution was stirred further for 6 hours at RT. Upon removal of the solvent in vacuo, the resulting mixture was taken into ethyl acetate and washed with 1 N HCl (2×30 ml), water (2×30 ml) and brine (2×30 ml). The organic layer was dried over anhydrous Na$_2$SO$_4$ and concentrated in vacuo to afford a white solid, which was further purified by flash chromatography (silica gel, dichloromethane/ethanol=9:1) to afford 1 (0.15 g, 56%). $^1$H NMR (300 MHz, CDCl$_3$) δ 7.67 (d, J=9.0 Hz, 1H), 7.27-7.23 (m, 7H), 6.38 (s, 1H), 4.1 (s, 2H), 3.73 (s, 2H), 2.91 (s, 2H), 2.32 (s, 3H). MS (ESI): m/z 448.0 [(M+Na)]$^+$.

Preparation of 4-(3,6-diacetoxy-3H-xanthen-9-yl)-isophthalic acid (13): Resorcinol 11 (5.7 g, 52 mmol) was dissolved in 50 ml of CH$_3$SO$_3$H. To this solution, trimellitic anhydride (5 g, 26 mmol) was added, and the reaction was heated at 80-85° C. for 12 hours. The highly viscous solution was cooled to RT then poured into 10 volumes of ice-cold water. The resulting precipitate was collected and dried in vacuo to give compound 12 as a crude yellow solid, which was used without further purifications. Compound 12 was dissolved in 50 ml of acetic anhydride and 10 ml of pyridine. The solution was heated at 85° C. for 15 minutes. The resulting solution was poured into ice-cold water to give the crude precipitate of 13, which, upon recrystallization with DCM, afforded pure 13 as white crystals (5.17 g, 53%).
$^1$H-NMR (300 MHz, CDCl$_3$) δ 8.75 (s, 1H), 8.38 (d, J=8.04 Hz, 1H), 7.29 (d, J=8.04, 1H), 7.15-7.09 (m, 2H), 6.85-6.81 (m, 4H), 2.31 (s, 6H). $^{13}$C-NMR (60 MHz, CDCl$_3$) δ 168.71, 167.46, 165.85, 155.48, 152.12, 150.69, 133.24, 132.47, 130.31, 129.23, 128.45, 126.14, 115.48, 110.41, 109.30, 81.21, 19.85. MS (ESI): m/z 461 [(M+1)]$^+$.

Preparation of N-benzylsulfanylcarbonylmethyl-6-(3,6-dihydroxy-3H-xanthen-9-yl)-isophthalamic acid (FL) (2): To a solution of 13 (0.424 g, 0.92 mmol) in dry THF was added EDC (0.176 g, 0.92 mmol) and HOBt (0.14 g, 0.92 mmol). The solution was stirred for 30 minutes under ice-cold conditions, followed by addition of 8 (0.2523 g, 1.16 mmol) dissolved in minimal amount of DMF. The resulting solution was stirred further for 6 hours at RT. Upon removal of the solvent in vacuo, the residue was taken into ethyl acetate and washed with 1 N HCl (2×30 ml), water (2×30 ml) and brine (2×30 ml). The organic layer was dried over anhydrous Na$_2$SO$_4$ and concentrated under reduced pressure to afford a crude mixture, which was further purified by flash chromatography (silica gel, dichloromethane/methanol=9:1) to afford 2 (0.32 g, 56%). $^1$H-NMR (300 MHz, CDCl$_3$) δ 8.52 (s, 1H), 8.22 (d, J=8.04 Hz, 1H), 7.25-7.21 (m, 6H), 7.12-7.09 (m, 2H), 6.81-6.75 (m, 4H), 4.39 (d, J=5.61 Hz, 2H), 4.15 (s, 2H), 2.3 (s, 6H). $^3$C-NMR (60 MHz, DMSO) δ 196.52, 168.78, 168.37, 165.84, 155.31, 152.20, 151.42, 136.72, 134.08, 129.58, 127.74, 127.50, 127.33, 126.45, 125.61, 124.50, 123.91, 115.53, 110.46, 82.09, 49.48, 32.90, 20.98. MS (ESI): m/z 623.9 [(M+1)]$^+$.

Preparation of 5-carboxy-tetramethylrhodamine (15): Trimellitic anhydride (1.00 g, 5.2 mmol) and 3-dimethylaminophenol, 14 (0.72 g, 10.5 mmol) was refluxed in toluene (50 ml) for 12 hours. Upon cooling to RT, the resulting precipitate was collected by filtration, and further purified by flash chromatography (silica gel, dichloromethane/methanol/acetic acid=8:1.9:0.1) to afford pure 15 as a dark purple solid (0.811 g, 36%). $^1$H-NMR (300 MHz, CDCl$_3$) δ 8.52 (s, 1H), 8.12 (d, J=8.61 Hz, 1H), 7.59 (d, J=7.62 Hz, 1H), 6.82 (m, 2H), 6.51 (d, J=5.61 Hz, 2H). 6.09 (s, 2H), 3.28 (s, 12H). MS (ESI): m/z 431.2 [(M+1)]$^+$.

Preparation of amino thioacetic acid S-benzyl ester of 5-carboxy-tetramethylrhodamine (TMR) (3): To a solution of 15 (0.05 g, 0.116 mmol) in dry THF was added EDC (0.022 g, 0.116 mmol) and HOBt (0.018 g, 0.116 mmol). The solution was stirred for 30 minutes under ice-cold conditions, followed by addition of 8 (0.025 g, 0.116 mmol) dissolved in minimal amount of DMF. The resulting solution was stirred further for 6 hours at RT. Upon removal of the solvent in vacuo, the residue was taken into ethyl acetate and washed with 1 N HCl (2×30 ml), water (2×30 ml) and brine (2×30 ml). The organic layer was dried over anhydrous $Na_2SO_4$ and concentrated under reduced pressure to afford a crude mixture, which was further purified by flash chromatography (silica gel, dichloromethane/ethanol=9:1) to afford 3 (0.024 g, 35%) as a dark purple solid. $^1$H-NMR (300 MHz, $CD_3OD$) δ 8.78 (s, 1H), 8.27 (d, J=8.01 Hz, 1H), 7.55 (d, J=7.83 Hz, 1H), 7.28 (d, J=6.45, 2H), 7.20-7.26 (m, 5H), 7.09-6.99 (m, 4H), 4.40 (s, 2H), 4.15 (s, 2H), 3.30 (s, 12H). MS (ESI): m/z 594.2 [(M+1)]$^+$.

Preparation of acetoxynapthofluorescein (18): Trimellitic anhydride (1.93 g, 10 mmol) was dissolved in $CH_3SO_3H$ (1 M). 16 (3.2 g, 20 mmol) was added and the solution was heated at 100° C. for 12 hrs. Upon cooling to RT, the solution was poured into 8 volumes of ice-cold water. The resulting red precipitate was collected and dried in vacuo to give crude 17, which was used directly without further purifications. MS (ESI): m/z 477.4 [(M+1)]$^+$. Crude 17 was dissolved in 50 ml of acetic anhydride and 10 ml of pyridine. The resulting mixture was heated at 80-90° C. for 15 minutes. Upon concentration to dryness, the residue was taken into ethyl acetate and washed with 1 N HCl (2×50 ml), water (2×50 ml) and brine (2×50 ml). The organic layer was dried over anhydrous $Na_2SO_4$, and concentrated in vacuo to give crude 18 (46% yield for 2 steps based on the crude product), which was confirmed by MS ((ESI): m/z 561.0 [(M+1)]$^+$) and used without further purifications.

Preparation of amino thioacetic acid S-benzyl ester of acetoxynapthofluorescein (CF) (4): To a THF solution of crude 18 (0.065 g, 0.116 mmol), obtained from above reaction, was added EDC (0.022 g, 0.116 mmol) and HOBt (0.018 g, 0.116 mmol). The solution was stirred for 30 minutes under ice-cold conditions, followed by addition of 8 (0.025 g, 0.116 mmol) dissolved in minimal amount of DMF. The resulting solution was stirred further for 6 hours at RT. Upon removal of the solvent in vacuo, the residue was taken into ethyl acetate and washed with 1 N HCl (2×30 ml), water (2×30 ml) and brine (2×30 ml). The organic layer was dried over anhydrous $Na_2SO_4$ and concentrated under reduced pressure to afford a crude mixture, which was further purified by reverse phase HPLC to afford pure 4 (0.025 g, 30% yield). $^1$H-NMR (300 MHz, $CDCl_3$) δ 8.62 (s, 1H), 8.22 (d, J=6.42 Hz, 1H), 8.14-8.11 (m, 2H), 7.64 (s, 2H), 7.48 (d, J=8.03 Hz, 1H), 7.31-7.27 (m, 9H), 7.19 (d, J=7.62 Hz, 2H), 4.2 (d, J=6.0 Hz, 2H), 4.01 (s, 2H), 2.37 (s, 6H). MS (ESI): m/z 724.1 [(M+1)]$^+$.

Preparation of [5-(2-oxo-hexahydro-thieno[3,4-d]imidazol-6-yl)-pentanoylamino]-thioacetic acid S-benzyl ester (5): Biotin 19 (0.156 g, 0.64 mmol) was dissolved in 40 mL of dry THF. To this solution was added EDC (0.123 g, 0.64 mmol) and HOBt (0.098 g, 0.64 mmol) under ice-cold conditions. The reaction was allowed to stir for 30 minutes, followed by addition of 8 (0.139 g, 0.64 mmol) dissolved in minimal amount of DMF. The resulting solution was allowed to stir overnight at RT. Upon removal of the solvent in vacuo, the residue was taken into ethyl acetate and washed with 1 N HCl (2×30 ml), water (2×30 ml) and brine (2×30 ml). The organic layer was dried over anhydrous $Na_2SO_4$ and concentrated under reduced pressure to afford 5 (0.110 g, 42%). $^1$H-NMR (300 MHz, DMSO) δ 7.31-7.28 (m, 5H), 6.40-6.35 (broad, 2H), 4.37-4.32 (m, 2H), 4.22 (d, J=5.61 Hz, 2H), 4.09 (s, 2H), 3.1-3.0 (m, 1H), 2.88-2.78 (m, 2H), 2.19-2.14 (m, 2H), 1.60-1.48 (m, 6H). MS (ESI): m/z 408.0 [(M+1)]$^+$.

Preparation of (4-benzoyl-benzoylamino)-thioacetic acid S-benzyl ester (6): To a solution of 20 (0.136 g, 0.6 mmol) in dry THF (40 ml) was added EDC (0.115 g, 0.6 mmol) and HOBt (0.092 g, 0.6 mmol). The solution was stirred for 30 minutes under ice-cold conditions, followed by addition of 8 (0.136 g, 0.6 mmol) dissolved in minimal amount of DMF. The resulting solution was stirred further for 6 hours at RT. Upon removal of the solvent in vacuo, the residue was taken into ethyl acetate and washed with 1 N HCl (2×30 ml), water (2×30 ml) and brine (2×30 m). The organic layer was dried over anhydrous $Na_2SO_4$ and concentrated under reduced pressure to afford a white solid, which was further purified by flash chromatography (silica gel, dichloromethane/ethanol=9.5:0.5) to afford 6 (0.157 g, 68%). $^1$H-NMR (300 MHz, $CDCl_3$) δ 7.94-7.91 (m, 2H), 7.76-7.73 (m, 4H), 7.61-7.56 (m, 1H), 7.48-7.43 (m, 2H), 7.27-7.20 (m, 5H), 4.37 (d, J=5.64 Hz, 2H), 4.12 (s, 2H). $^{13}$C-NMR (60 MHz, $CDCl_3$) 195.88, 194.66, 166.68, 140.39, 138.69, 136.66, 134.20, 132.89, 131.82, 131.17, 130.05, 129.99, 128.99, 128.80, 128.23, 128.16, 127.45, 127.38, 127.10, 49.39, 33.00. MS (ESI): m/z 389.47 [(M+1)]$^+$.

Preparation of 2-nitrobenzyl tosylate (22): 2-Nitrobenzyl alcohol (1 g, 6.5 mmol) was dissolved in 40 ml of dry DCM and 1.36 ml of triethylamine. p-toluenesulfonyl chloride (1.24 g, 6.5 mmol) was added and the solution was stirred for 2 hours before quenching with water. The organic layer was separated and washed with 1 N HCl (1×50 ml), water (1×50 ml), 2 N NaOH (1×50 ml), water (1×50 ml) and brine (1×50 ml). The organic layer was dried over anhydrous $Na_2SO_4$ and concentrated under reduced pressure to give a dull white solid, which was further purified by flash chromatography (silica gel, dichloromethane/ethanol=9.5:0.5) to give 2-nitrobenzyl tosylate, 22 (1.57 g, 79%). $^1$H-NMR (300 MHz, $CDCl_3$) δ 8.08-7.99 (dd, J=9.21 & 8.04 Hz, 1H), 7.81 (d, J=8.4 Hz, 1H), 7.72-7.62 (m, 3H), 7.50 (d, J=8.85 Hz, 1H) 7.33 (d, J=8.43 Hz, 2H), 4.93 (s, 2H), 2.42 (s, 3H). $^{13}$C-NMR (60 MHz, $CDCl_3$) δ 149.33, 146.12, 137.71, 135.27, 134.11, 133.09, 132.69, 132.57, 128.12, 123.89, 42.72, 20.64. MS (ESI): m/z 329.9 [(M+Na)]$^+$.

Preparation of "caged" fluorescein (C2FL) (23): Crude 12 was first purified by recrystallization. The recrystallized product (0.602 g, 1.6 mmol) was dissolved in 30 ml of DMF containing $K_2CO_3$ (1.1 g, 5 mmol). 2-nitrobenzyl tosylate (0.492 g, 1.6 mmol) was added to the solution and the reaction was heated at 60° C. for 6 hours in a RBF covered with aluminium foil to maintain dark conditions. After 6 hrs, the solvent was removed in vacuo and the residual mixture was washed with 1 N HCl, water and brine followed by drying in anhydrous $Na_2SO_4$ and concentration under reduced pressure to afford 23 (0.64 g, 62%). The work up was strictly done in dark. $^1$H-NMR (300 MHz, $CDCl_3$) δ 8.44 (s, 1H), 8.16 (d, J=8.11 Hz, 1H), 8.00-7.97 (m, 2H), 7.75-7.85 (m, 2H), 7.60-7.56 (m, 4H), 7.45 (d, J=8.10 Hz, 1H), 7.35 (d, J=7.86 Hz, 2H), 7.22-7.10 (m, 4H), 5.51 (s, 4H). MS (ESI): m/z 647.0 [(M+1)]$^+$.

Preparation of amino thioacetic acid S-benzyl ester of C2FL (7): The reaction and workups were carried out in dark. To a solution of 23 (0.084 g, 0.13 mmol) in dry THF was added EDC (0.027 g, 0.143 mmol) and HOBt (0.022 g, 0.143 mmol). The solution was stirred for 30 minutes under ice-cold conditions, followed by addition of 8 (0.028 g, 0.13 mmol) dissolved in minimal amount of DMF. The resulting solution was stirred further for 6 hours at RT. Upon removal of the solvent in vacuo, the residue was taken into ethyl acetate and washed with 1 N HCl (2×30 mm), water (2×30 ml) and brine (2×30 ml). The organic layer was dried over anhydrous $Na_2SO_4$ and concentrated under reduced pressure to afford a crude mixture, which was further purified by flash chromatography (silica gel, dichloromethane/ethanol=9.8:0.2) to afford 7 (0.040 g, 38%). $^1$H-NMR (300 MHz, $CDCl_3$) δ 8.38 (s, 1H), 8.29 (d, J=8.13 Hz, 1H), 8.08-8.11 (m, 2H), 7.99-7.90 (m, 2H), 7.71-7.68 (m, 4H), 7.65 (d, J=8.10 Hz, 1H), 7.60-7.49 (m, 6H), 7.25 (s, 5H), 5.29 (s, 4H), 4.68 (s, 2H), 4.19 (s, 2H). MS (ESI): m/z 810.1 [(M+1)]$^+$.

Figure 5:
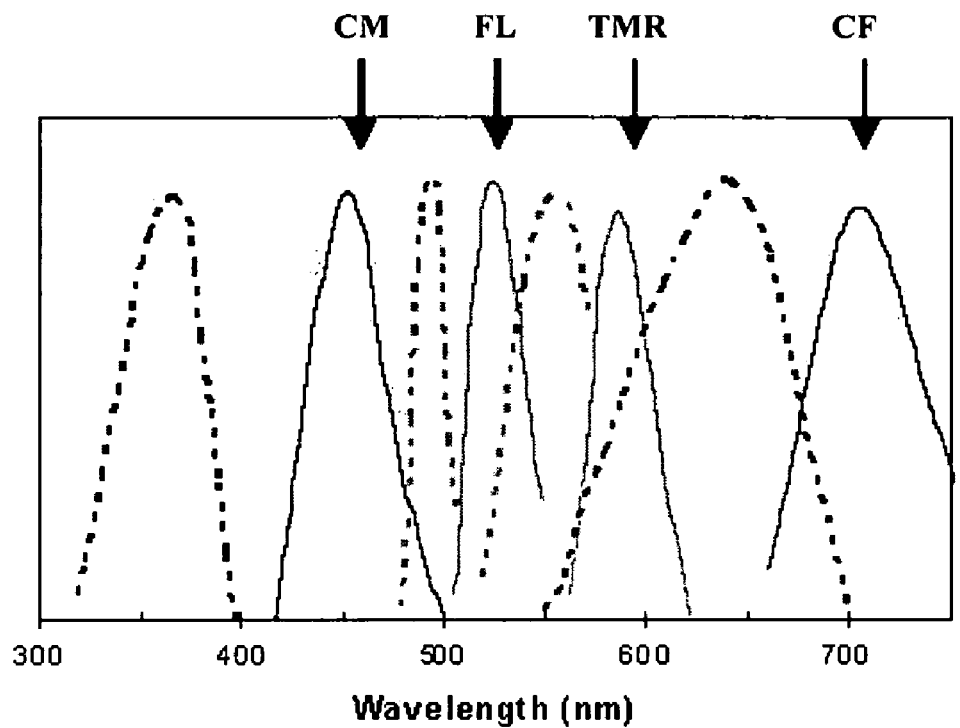
FIG. 5 is a fluorescence spectra of probes 1 (CM), 2 (FL), 3 (TMR), and 4 (CF)

Probes 1 to 4, containing different fluorophores (e.g. coumarin (CM), fluorescein (FL), TMR and carboxynaphthofluorescein (CF), respectively) that emit in different colors (e.g. blue, green, orange/yellow and red, respectively), were designed for potential multicolor cell labelling and imaging. FIG. 5 shows the fluorescence spectra obtained (excitation and emission spectra are shown by dashed and solid lines, respectively). Fluorescence experiments were performed by adding 10 μl each of the stock solutions of probes 1, 2, 3 and 4 (1 mM in DMSO) to 100 μl of 1 mM $K_2CO_3$ solution, and allowing the mixture to stand at RT for >5 min for the deacylation reaction to occur, resulting in the release of very strong fluorescence in the solution. 10 μl of the solution was subsequently diluted with 100 μl of distilled water, and the resulting solution was transferred to a black 96-well microtitre plate (Nunc, USA), where the excitation and the emission spectra of the probes were recorded using a SpectraMax™ GeminiXS fluorescence microplate reader (Molecular Devices, USA).

Proteins labelled with probes 5 and 6 may be used to study protein-protein interactions by in vivo experiments utilizing biotin-avidin binding and protein crosslinking, respectively.

Probe 7 may be selectively photolysed, making it useful for protein labelling in a live cell where temporal and/or confined fluorescence activation is needed (J. P. Schwartz and G. H. Patterson, *Science* (2003) 300: 87).

Example 2

In vitro Labelling of Proteins Expressing an N-Terminal Cysteine

A model protein, EGFP (enhanced green fluorescent protein), engineered to contain an N-terminal cysteine, was incubated with probes 2, 3, 4 and 5 individually to assess the labelling strategy.

Probes were prepared as 200 μM stocks (25× in DMSO) and stored at −20° C. In a typical labelling reaction, 6 μl of each probe (final concentration: 8 μM) was added to 50 μl of pure protein (1 mg/ml) dissolved in 1×PBS (final concentration of protein: ~2 nM), with or without 1 mM DTT, and the reaction was topped up with 1×PBS to a final volume of 150 μl. DTT was added to experiments, where live cells were used, to reduce background labelling. At specific time intervals, 15 μl of the reaction was withdrawn and quenched by addition of 1.7 μl of 100 mM cysteine to the reaction mixture (final concentration of cysteine: 10 mM), followed by denaturation with SDS-PAGE loading dye at 95° C. for 3 min. The loading dye also serves to hydrolyze the diacetate groups on probes 2 and 4, thereby releasing the fluorescence.

The extent of protein labelling was monitored over 24 hours by SDS-PAGE and Western blotting. Upon separation with a 12% SDS-PAGE gel, the fluorescence labelling of EGFP by probes 2, 3 and 4 was conveniently visualized by scanning the resulting gel with a Typhoon™ 9200 fluorescence scanner (Amersham Biosciences, USA). Fluorescence intensity of each protein band was analysed using the software, Image Quant 5.2, preinstalled on the instrument. In all cases, more than 75% of labelling was obtained in 3 hours for all three probes. For the labelling of EGFP with probe 5, an anti-biotin Western blot was performed to visualize the amount of biotinylated EGFP.

Briefly, following SDS-PAGE separation, the resulting gel was electroblotted onto a polyvinylidene difluoride (PVDF) membrane (BioRad, USA) and blocked for 1 h with 5% non-fat dry milk in PBST (phosphate buffered saline, pH 7.4 with 0.1% Tween 20). The membrane was incubated with anti biotin-conjugated HRP (NEB, USA) in a 1:3000 dilution in milk-PBST for 1 h and then washed with PBST (3×15 min). Visualization was done with the Enhanced ChemiLuminescent ECL™ kit (Amersham).

The reaction was quenched at specified time intervals with 10 mM of cysteine. Following protein separation on a 12% SDS-PAGE gel, the labelled protein was visualized and quantified, either by a fluorescence gel scanner (in cases with probes 2, 3 and 4) or western blotting using anti-biotin HRP conjugate and Amersham's ECL kit (in the case with probe 5).

Figure 6:
FIG. 6 is a fluorescence photograph of an SDS-PAGE gel of N-terminal cysteine EGFP protein labelled in vitro with probe 2.
Figure 7:
FIG. 7 is a fluorescence photograph of an SDS-PAGE gel of N-terminal cysteine EGFP protein labelled in vitro with probe 3.
Figure 8:
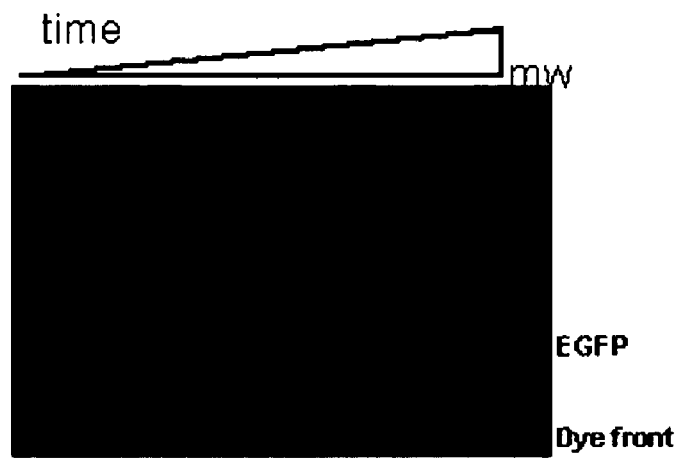
FIG. 8 is a fluorescence photograph of an SDS-PAGE gel of N-terminal cysteine EGFP protein labelled in vitro with probe 4.
Figure 9:
FIG. 9 is a photograph of a Western blot of N-terminal cysteine EGFP protein labelled in vitro with probe 5.
Figure 10:
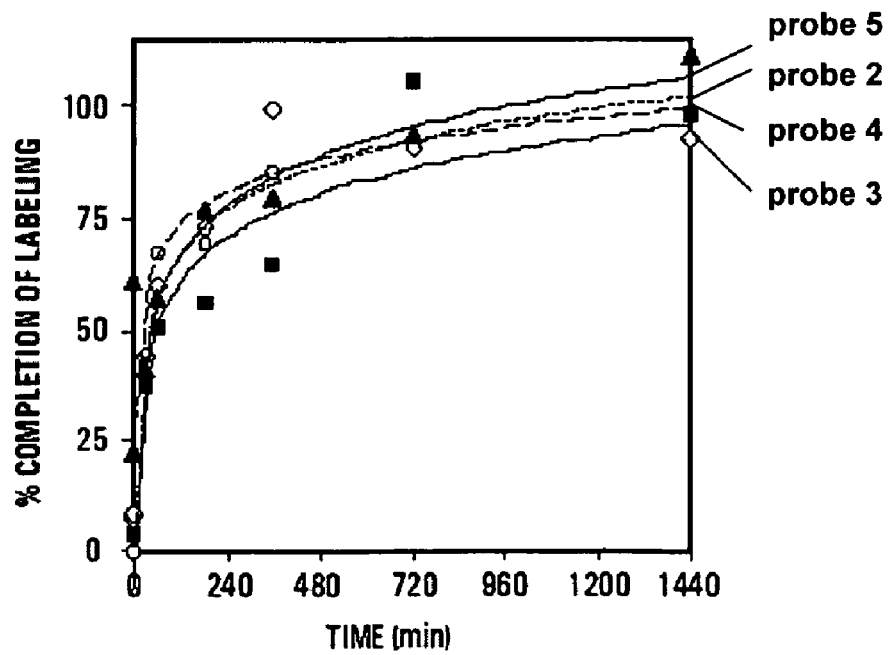
FIG. 10 is a graph illustrating the percent completion of EGFP in vitro labelling over a 24 hour time course with probes 2 to 5.

SDS-PAGE and Western blot results are visualized in FIGS. 6-9 (lanes 1-8 are samples taken at 1 min, 10 min, 30 min, 1 h, 3 h, 6 h, 12 h and 24 h, respectively, and lane 9 in FIG. 6 contains molecular weight markers). In all cases, the labelling was shown to reach near completion (>75% labelling) within the first 3 hours of the reaction, as indicated in FIG. 10 (probe 2=◇, probe 3=■, probe 4=▲ and probe 5=□). In addition, more than 50% labelling occurred within the first 30 min of the reaction, making this strategy suitable for potential real-time bioimaging experiments in live cells.

Figure 11:
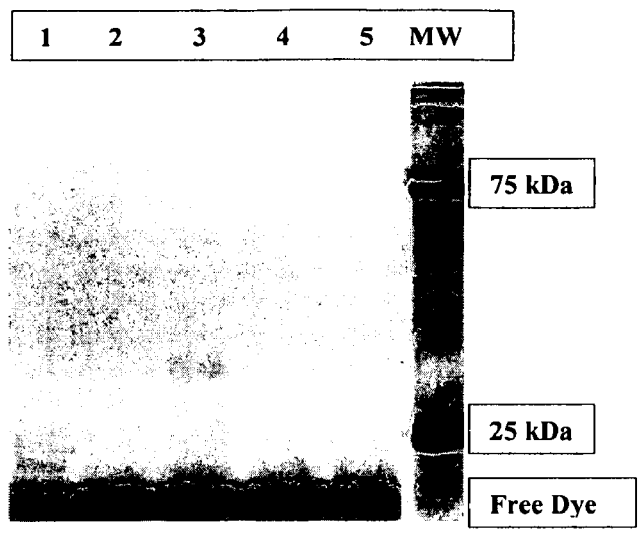
FIG. 11 is a fluorescence photograph of an SDS-PAGE gel in vitro labelling reactions using probe 3 to label commercially available proteins without an N-terminal cysteine.

The site-specific nature of the labelling reaction was confirmed by repeating the experiment under identical conditions with 5 control proteins which either do not have cysteine residues at all, or have only internal cysteines. In all cases, labelling occurred ONLY with proteins possessing an N-terminal cysteine, as seen in FIG. 11. Probe 3 was used in the labelling reaction, and the reaction was performed as mentioned above with 60 min incubation time. All proteins are available from Sigma (St Louis, USA). (Lane 1. GST (cat #: G-4385); Lane 2. Protease (P-5380); Lane 3. Lipase (L-9031); Lane 4. Papain (P-4762); Lane 5. Pepsin (P-6887); Lane 6. BioRad Precision Plus Protein Standards). These results support the design principle in which exclusive labelling should only occur at the N-terminal cysteine of the target protein.

Example 3

In vivo Labelling of N-Terminal Cysteine Proteins in Bacterial Cells

The strategy was next applied to the labelling of N-terminal cysteine proteins expressed inside live bacterial cells.

Two model proteins, EGFP (enhanced green fluorescent protein) and GST (gluthathione-S-transferase), were PCR amplified from pEGFP (Clontech, USA) and pGEX-4T1 (Pharmacia Biotech, USA), respectively, and cloned into the pTWIN1/2 expression vector (NEB, USA) downstream of the C-terminus the Ssp DnaB intein tag. The genes were inserted between the first SapI site and the PstI site on the vector, with a cysteine introduced by PCR as the first amino acid of the target protein, generating pTWIN1-EGFP and pTWIN2-GST, respectively. PCR primers used for pTWIN1-EGFP were 5'-GGT GGT TGC TCT TCC AAC TGC AGA GCC ATG GTG AGC AAG GGC-3' [SEQ ID NO:1] and 5'-GGT GGT CTG CAG TTA CTT GTA CAG CTC GTC-3'

[SEQ ID NO:2]. PCR primers used for pTWIN2-GST were 5'-GGT GGT TGC TCT TCC AAC TGC AGA GCC ATG TCC CCT ATA CTA-3' [SEQ ID NO:3] and 5'-GGT GGT CTG CAG TCA GTC ACG ATG CGG-3' [SEQ ID NO:4].

To generate in vivo proteins having N-terminal cysteine residues, bacterial cells expressing N-terminal cysteine-containing proteins EGFP and GST fused to the C-terminus of the Ssp DnaB mini-intein were induced to undergo self-cleavage, releasing the N-terminal cysteine protein, then incubated with the probes over a period of 24 h. None of the probes showed cell toxicity even at mmol concentrations.

Figure 12:
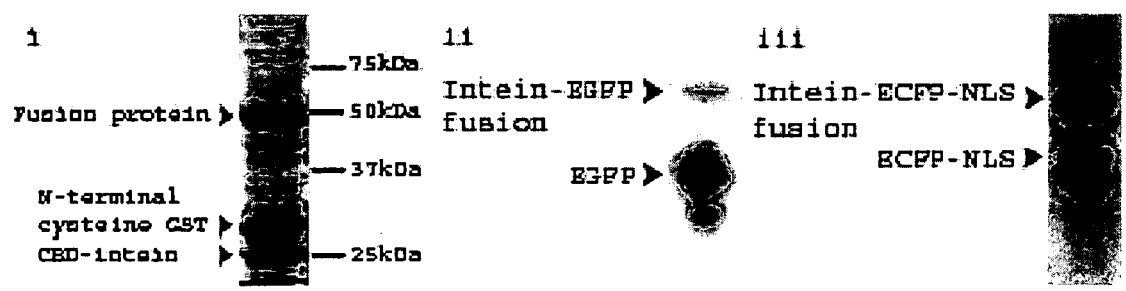
FIG. 12 is a photograph of an SDS-PAGE gel (i.) and Western blots (ii. and iii.) demonstrating the generation of cleaved N-terminal cysteine GST in bacterial cells, and N-terminal cysteine EGFP and N-terminal cysteine ECFP in mammalian cells, respectively.

Briefly, the above bacterial constructs were transformed into the *E. coli* expression strain ER2566 (NEB) and grown in 100 mg/L ampicillin containing LB media at 37° C. At $OD_{600}=\sim0.6$, 0.3 mM of IPTG (isopropyl-β-D-thiogalactoside) was added, and the cells were further grown for 12 h at room temperature to induce the fusion protein expression, as well as for the fusion protein to undergo self-cleavage and generate the desired N-terminal cysteine protein in vivo (see FIG. 12*i*.).

To label the protein in live cells, 20 μM of the relevant probe (5-100 μM also worked) was added directly to the LB media containing grown cells, and incubated for 24 h.

For the time-course labelling experiments, a small sample of cells was removed at each time interval, quenched with 0.01M cysteine, and lysed by boiling with SDS loading buffer. The resulting sample was analyzed directly on a 12% SDS-PAGE. Fluorescence labelling was visualized with a Typhoon™ fluorescence scanner (Amersham Biosciences). Biotinylated proteins were detected by western blotting (with anti-biotin-HRP) with the Enhanced ChemiLuminescent™ kit (Amersham).

Figure 13:
FIG. 13 is a photograph of SDS-PAGE gels and a Western blot of N-terminal cysteine GST protein labelled in vivo in live bacterial cells with i. probe 2 (FL), ii. probe 3 (TMR) and iii. probe 5 (BIOTIN)
Figure 14:
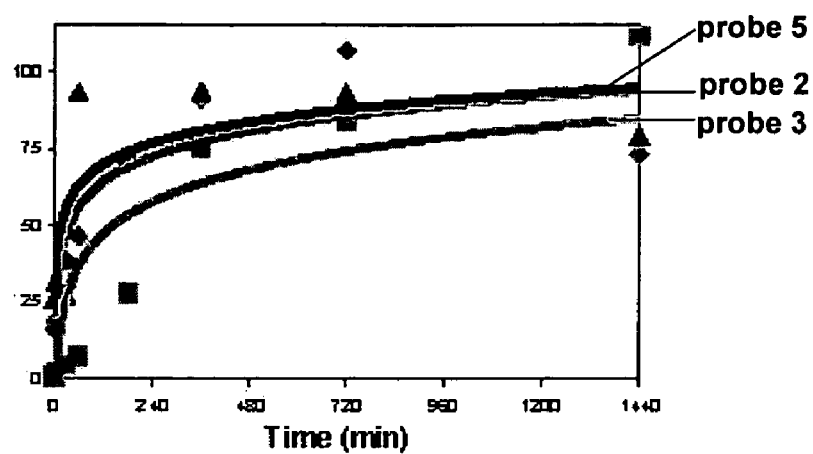
FIG. 14 is a graph illustrating the percent completion of N-terminal cysteine GST in vivo labelling over a 24 hour time course with probes 2, 3 and 5.
Figure 15:
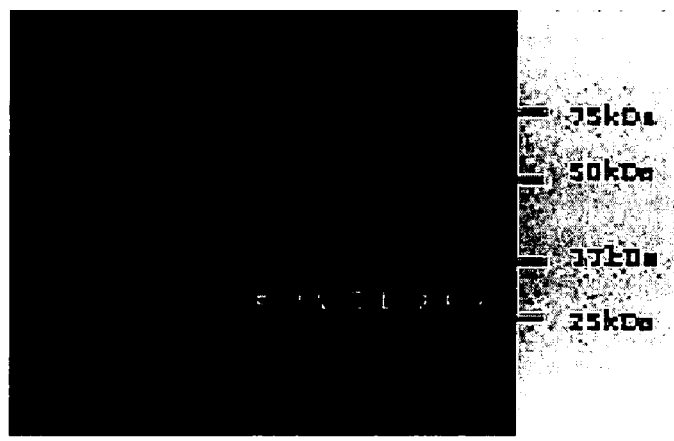
FIG. 15 is a fluorescence photograph of an SDS-PAGE gel of N-terminal cysteine GST protein labelled in vivo in live bacterial cells with probe 2 (FL)

As previously observed for in vitro labelling, in vivo labelling was shown to occur in a time-dependent fashion, with >50% of the labelled protein observed within the first 3 h of labelling. Results are shown in FIG. 13, where i=cells labelled with probe 2 (FL), ii=cells labelled with probe 3 (TMR) and iii=cells labelled with probe 5 (biotin) (lanes 1-8 are samples taken at 0 min, 10 min, 30 min, 1 h, 3 h, 6 h, 12 h and 24 h, respectively). The results of the 24 hour time-course are quantified in FIG. 14 (FL=◆, TMR=■ and BIOTIN=▲). SDS-PAGE analysis of cells expressing FL-labelled GST, sampled at the same times as for FIG. 13, further demonstrate that only the desired protein was labelled specifically, as well as covalently, inside the live cell, with little or no background observed (FIG. 15).

For fluorescence microscopy experiments, labelled cells were harvested by centrifugation at 4000 rpm for 10 min. Upon resuspension in 1×PBS buffer (pH 7.4) containing 10% glycerol, the cells were left standing for 30 min. This procedure was repeated 3 times for complete removal of any free probe. Cells were mounted on clean glass slides coated with 1.5% agarose. Fluorescence images were recorded with the AxioSkop™ 40 fluorescence microscope (Zeiss, Germany) equipped with a cooled CCD camera (AxioCam, Zeiss) using a 63× or 100× oil objective. Different fluorescence images were obtained with different excitation/emission filter sets: Coumarin channel (excitation=365+20 nm and emission=420 nm LP); CFP channel (excitation=436±20 nm and emission=480±40 nm); GFP channel (excitation=470±20 nm and emission=530±25 nm); TMR & Red channels (excitation=546±12 nm and emission=590 nm LP). The FRET channel for CFP/TMR pair was recorded using filters with an excitation: 436±20 nm and emission: 620±20 nm (Chroma). The FRET channel for GFP/TMR pair was using filters with excitation=470±20 nm and emission=605±30 nm (Zeiss).

Figure 16:
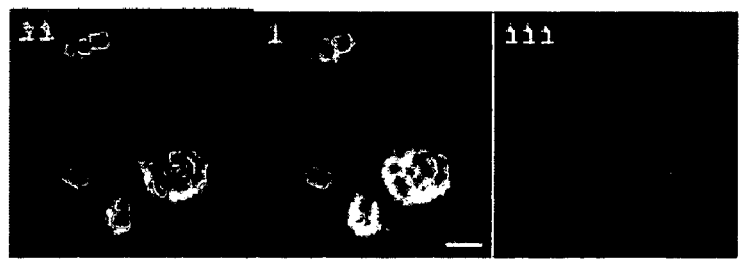
FIG. 16 is microscopy photographs of bacterial cells with N-terminal cysteine EGFP labelled with probe 3 (TMR)
Figure 17:
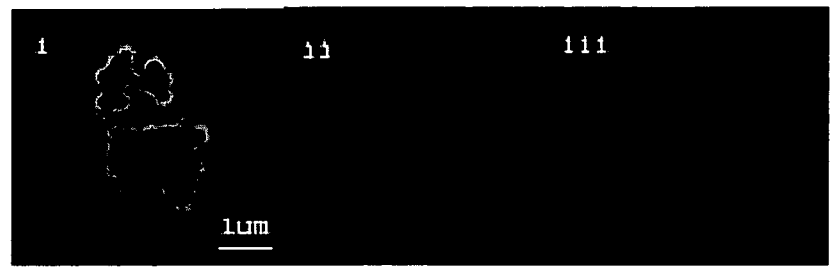
FIG. 17 is fluorescence microscopy photographs of unlabelled bacterial cells expressing N-terminal cysteine EGFP.

Fluorescence microscopy of the bacterial cells expressing labelled protein indicate that the labelling only occurred with cells expressing the desired protein, as indicated by a comparison of FIGS. 16 and 17 (FIG. 16: EGFP-expressing cells labelled with probe 3: i. overlay of phase contrast image with fluorescence microscopy image (GFP channel); ii. overlay of phase contrast image with fluorescence microscopy image (TMR channel); iii. FRET channel of the labelled cells (excitation: 470±20 nm; emission: 605±30 nm). FIG. 17: unlabelled cells expressing N-terminal cysteine EGFP: i. GFP channel; ii. FRET channel under the same exposure conditions as in FIG. 16*iii*; iii. FRET channel with a 10× longer exposure time). The spectra overlap of EGFP and probe 3 in the labelling strategy provided an ideal donor-acceptor pair for fluorescence resonance energy transfer (FRET), which only occurs when both donor and acceptor are in close proximity (Griffin, B. A., Adams, S. R., & Tsien, R. Y. *Science* (1998) 281: 269-272). This serves to confirm the covalent labelling of the N-terminal cysteine proteins with the probes inside live cells. As shown in FIG. 16, a clear FRET signal was observed in all probe 3-labelled bacterial cells expressing EGFP, indicating the covalent nature of the labelling. A negative control of unlabelled cells expressing EGFP revealed no fluorescence in the FRET channel even with extended exposure time.

Figure 18:
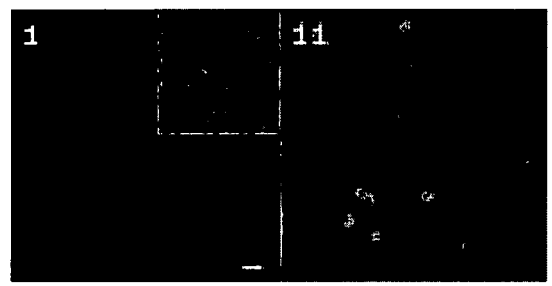
FIG. 18 is fluorescence microscopy photographs of bacterial cells with N-terminal cysteine GST labelled with probe 7 (C2FL)
Figure 19:
FIG. 19 is fluorescence microscopy photographs of i. bacterial cells not expressing N-terminal cysteine GST but labelled with probe 3 (TMR); and bacterial cells with N-terminal cysteine GST labelled with ii. probe 1 (CM), iii. probe 2 (FL) and iv. probe 4 (CF)

The versatility of the strategy was demonstrated by labelling live cells with probes having different fluorescence and other chemical properties (FIGS. 18 and 19). Bacterial cells expressing N-terminal cysteine GST were labelled with probes 1-4 (CM, FL, TMR and CF, respectively), giving rise to cells that have different "colors" (FIG. 19; i. fluorescence microscopy image (TMR channel) of negative control with cells not expressing N-terminal GST but labelled with TMR (insert: phase contrast image); ii. fluorescence microscopy image (blue channel) of GST-expressing cells labelled with CM; iii. fluorescence microscopy image (GFP channel) of GST-expressing cells labelled with FL; iv. fluorescence microscopy image (Red channel) of GST-expressing cells labelled with CF). When labelled with probe 7 (C2FL), the caged analog of FL, labelled proteins inside the cell could be selectively "lit" up by UV photolysis (FIG. 18; i. fluorescence microscopy image (GFP channel) after 0 min UV photolysis (insert: phase contrast image); ii. fluorescence microscopy image (GFP channel) after 5 min UV photolysis), indicating the potential of this approach for other advanced bioimaging techniques. The probe 5-labelled proteins (biotin) are suitable for in vivo studies of protein-protein interactions by pull-down experiments.

Example 4

In vivo Labelling of N-Terminal Cysteine Proteins in Mammalian Cells

Having successfully demonstrated the strategy for highly specific, covalent protein labelling inside bacterial cells, the strategy was extended to mammalian HEK293 cells, which are more useful for bioimaging applications, yet much more challenging because of their cellular complexity.

Intein-fused EGFP and ECFP (enhanced cyan fluorescent protein) were constructed, in which an extra N-terminal cysteine was introduced into both EGFP and ECFP, as described above. To facilitate evaluation of the labelling, as well as to assess whether the strategy targets proteins expressed in subcellular compartments of mammalian cells (e.g. nucleus), a nuclear localization sequence (NLS) was fused to ECFP, generating ECFP-NLS. The intein-fused EGFP gene was amplified from the above bacterial construct, while the ECFP gene with a nuclear localization sequence (ECFP-NLS) was amplified from pECFP-Nuc (Clontech, USA) and cloned first into the pTWIN1 vector. Using the GATEWAY™ cloning system (Invitrogen, USA), the intein-fused genes were cloned into the donor vector pDONR201, followed by recombination of the cloned genes into a mammalian expression vector pT-Rex-DEST30 (Invitrogen). All constructs were sequence verified. The PCR primers used for the mammalian construct pT-Rex-DEST30-intein/EGFP were 5'-GGGG ACA AGT TTG TAC AAA AAA GCA GGC TTC GAA GGA GAT AGA ACC ATG GCT ATC TCT GGC GAT AGT-3' [SEQ ID NO: 5] and 5'-GGGG AC CAC TTT GTA CAA GAA AGC TGG GTC CTG CAG TTA CTT GTA CAG-3' [SEQ ID NO: 6]. The PCR primers used for the mammalian construct pT-Rex-DEST30-intein/ECFP-NLS were 5'-GGT GGT CTG CAG TTA TCT AGA TCC GGT GGA-3' [SEQ ID NO: 7] and 5'-GGGG AC CAC TTT GTA CAA GAA AGC TGG GTC CTG CAG TTA TCT AGA TCC-3' [SEQ ID NO: 8].

Briefly, HEK293 cells grown in DMEM+10% FBS media at 37° C. with 5% $CO_2$ were transiently transfected with pT-Rex-DEST30-intein-EGFP-NLS or pT-Rex-DEST30-intein-ECFP-NLS using Polyfect™ (Qiagen, USA). See FIGS. 12*ii.* and *iii.*, respectively, for in vivo intein cleavage for the expressed EGFP and ECFP proteins expressed in HEK293 cells. After 36 hours of protein expression, cells were washed in 1×PBS and cystine-free DMEM (Sigma) was added. The biotin-thioester probe, probe 5, was added to a final concentration of 100 µM (10-100 µM also worked) and cells were incubated for another 24 h. No cell toxicity was observed. Cells were harvested by centrifugation at 1000 rpm for 10 min and resuspended in 1×PBS. Washings were repeated at least 3 times, and cells were lysed in PBS using glass beads. Magnetic streptavidin beads (Promega, USA) were used to pull-down all biotinylated proteins in the cell lysate. Beads were washed twice in 1× PBS, then boiled in 1×SDS loading buffer and loaded onto a 12% SDS-PAGE. Western blotting was used to assess biotinylated proteins, as described above.

Figure 20:
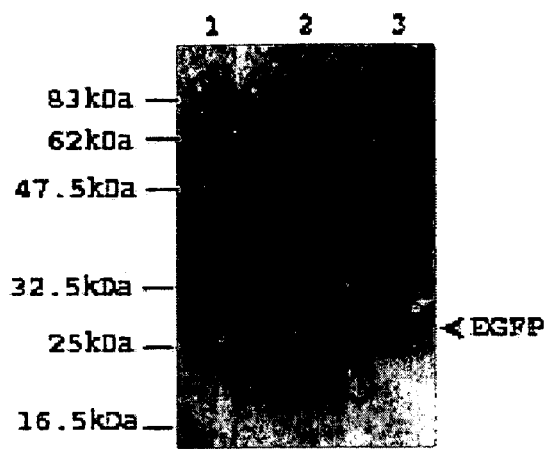
FIG. 20 is a photograph of a Western blot of mammalian cells with N-terminal cysteine EGFP labelled with probe 5 (BIOTIN)

Successful in vivo labelling of EGFP was observed by SDS-PAGE and Western blots of the resulting cell lysates (FIG. 20; lane 1. non-transfected cells; lane 2. non-transfected cells labelled with 100 µM of the probe; lane 3. EGFP-transfected cells labelled with 100 µM of the probe), confirming the covalent nature of the strategy. Untransfected cells, when labelled similarly with the probe, showed noticeable background labelling, which, fortunately was almost completely eliminated in EGFP-transfected cells. The only other major band besides the expected EGFP in labelled cells (see lane 3) was derived from endogenous biotinylated proteins, methyl-crotonylo-CoA-carboxylase and propionyl-CoA-carboxlyase (both 75 kDa), whose co-migrating band was also present in unlabelled cells (see lane 1), further validating the feasibility of the strategy in mammalian cells with tolerable background labelling.

Fluorescence microscopy experiments were also performed using HEK293 mammalian cells. Following their growth as described above to induce protein expression, cells were washed in 1×PBS and cystine-free DMEM (Sigma) was added, followed by 100 µM of probe 3 (10-100 µM also worked) and 0.01 mM $CaCl_2$. Upon incubation for 24 h, labelled cells were washed thrice with 1×PBS and imaged with the AxioVert™ 2000 fluorescence microscope (Zeiss) equipped with a cooled CCD camera (AxioCam™, Zeiss) using a 63× objective. The fluorescence images were obtained using the excitation and emission channels described above for the bacterial experiments.

Figure 21:
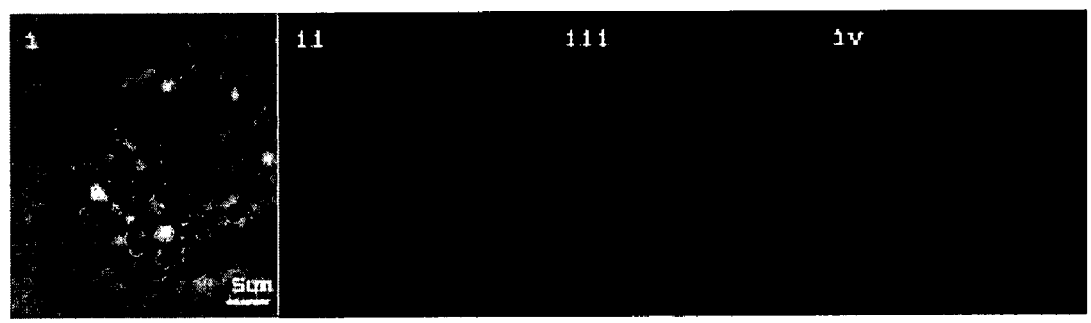
FIG. 21 is a fluorescence microscopy photographs of mammalian cells with N-terminal cysteine ECFP labelled with probe 3 (TMR)
Figure 22:
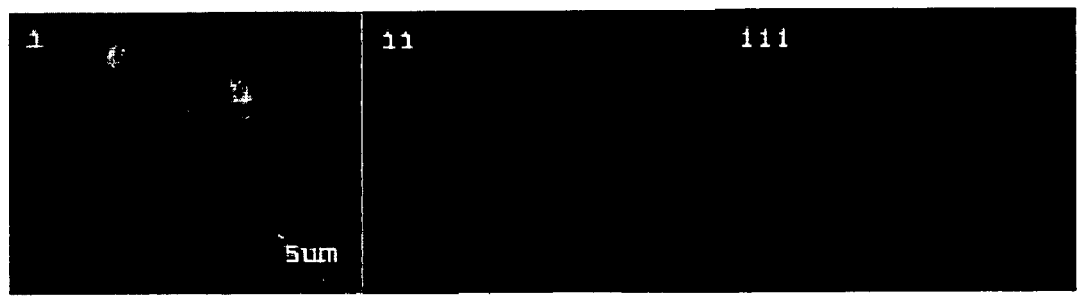
FIG. 22 is fluorescence microscopy photographs of unlabelled mammalian cells expressing N-terminal cysteine ECFP.

Fluorescence microscopy of cells transfected with ECFP-NLS revealed localization of the protein in the nucleus, as seen in FIG. 21 (i. phase contrast image; ii. fluorescence image (CFP channel); iii. fluorescence image (TMR channel); iv. FRET channel (excitation: 436±10 nm; emission: 620±30 nm)). Upon labelling with probe 3, it was observed that the majority of the labelling occurred inside the nucleus. Since ECFP and probe 3 form a FRET pair, the covalent labelling of the strategy was further confirmed by the observation of a clear FRET signal in the nucleus of the labelled cells. A negative control with unlabelled cells expressing ECFP-NLS showed no FRET signal under the same exposure time (FIG. 22; i. phase contrast image; ii. fluorescence image (CFP channel); iii. FRET channel under the same exposure as iv. in FIG. 21).

As can be understood by one skilled in the art, many modifications to the exemplary embodiments described herein are possible. The invention, rather, is intended to encompass all such modification within its scope, as defined by the claims.

What is claimed is:

1. A method for labelling a protein in a cell, comprising introducing a detectable probe having a thioester group into a cell expressing a protein that is proteolytically processed to expose an N-terminal cysteine; and washing the cell; wherein the probe is acetic acid 4-[(benzylsulfanylcarbonylmethyl-carbamoyl)-methyl]-2-oxo-2H-chromen-7-yl ester; N-benzylsulfanylcarbonylmethyl-6-(3,6-dihydroxy-3H-xanthen-9-yl)-isophthalamic acid; amino thioacetic acid S-benzyl ester of 5-carboxy-tetramethylrhodamine; amino thioacetic acid S-benzyl ester of acetoxynapthofluorescein; [5-(2-oxo-hexahydro-thieno[3,4-d]imidazol-6-yl)-pentanoylamino]-thioacetic acid S-benzyl ester; (4-benzoyl-benzoylamino)-thioacetic acid S-benzyl ester; or amino thioacetic acid S-benzyl ester of caged fluorescein, and is cell-permeable.

2. The method of claim 1 wherein said introducing the probe comprises adding the probe to the cell in a culture medium for about 1 to about 24 hours.

3. The method of claim 1 wherein said introducing the probe comprises adding the probe to the cell in a culture medium for about 3 to about 8 hours.

4. The method of claim 1 wherein the protein having an N-terminal cysteine is generated by intein-mediated protein cleavage.

5. The method of claim 1 wherein the protein having an N-terminal cysteine is generated by site-specific protelysis.

6. The method of claim 1 wherein the protein having an N-terminal cysteine is generated by de-ubiquination of a ubiquitin fusion protein.

7. A method for visualizing a protein in a cell, comprising introducing a detectable probe having a thioester group into a cell expressing a protein that is proteolytically processed to expose an N-terminal cysteine; washing the cell; and observing the cell under conditions in which the detectable probe may be visualized; wherein the probe is acetic acid 4-[(benzylsulfanylcarbonylmethyl-carbamoyl)-methyl]-2-oxo-2H-chromen-7-yl ester; N-enzylsulfanylcarbonylmethyl-6-(3,6-dihydroxy-3H-xanthen-9-yl)-isophthalamic acid; amino thioacetic acid S-benzyl ester of 5-carboxy-tetramethylrhodamine; amino thioacetic acid S-benzyl ester of acetoxynapthofluorescein; or amino thioacetic acid S-benzyl ester of caged fluorescein, and is cell-permeable and wherein said conditions comprise fluorescence microscopy.

8. The method of claim 7 wherein said introducing the probe comprises adding the probe to the cell in a culture medium for about 1 to about 24 hours.

9. The method of claim 7 wherein said introducing the probe comprises adding the probe to the cell in a culture medium for about 3 to about 8 hours.

10. The method of claim 7 wherein the protein having an N-terminal cysteine is generated by intein-mediated protein cleavage.

11. The method of claim 7 wherein the protein having an N-terminal cysteine is generated by site-specific proteolysis.

12. The method of claim 7 wherein the protein having an N-terminal cysteine is generated by de-ubiquination of a ubiquitin fusion protein.

\* \* \* \* \*